United States Patent
Kumar

(10) Patent No.: US 6,217,332 B1
(45) Date of Patent: Apr. 17, 2001

(54) COMBINATION IMPLANT CARRIER AND VIAL CAP

(75) Inventor: Ajay Kumar, Palmdale, CA (US)

(73) Assignee: Nobel Biocare AB, Gothenburg (SE)

( * ) Notice: Subject to any disclaimer, the term of this patent is extended or adjusted under 35 U.S.C. 154(b) by 0 days.

(21) Appl. No.: 09/303,699

(22) Filed: May 3, 1999

Related U.S. Application Data

(63) Continuation-in-part of application No. 09/227,069, filed on Jan. 5, 1999.
(60) Provisional application No. 60/092,674, filed on Jul. 13, 1998, and provisional application No. 60/092,649, filed on Jul. 13, 1998.

(51) Int. Cl.[7] .................................................... A61C 8/00
(52) U.S. Cl. ............................ 433/173; 206/368; 215/227
(58) Field of Search .................................... 433/172, 173, 433/174, 201.1; 206/83, 368, 369, 438; 215/227, DIG. 3

(56) References Cited

U.S. PATENT DOCUMENTS

| | | |
|---|---|---|
| 2,347,567 | 4/1944 | Kresse . |
| 3,346,135 * | 10/1967 | Haitsch ................. 215/227 |
| 3,481,712 * | 12/1969 | Bernstein et al. .......... 215/227 |
| 4,158,256 | 6/1979 | Wiland et al. . |
| 4,187,609 | 2/1980 | Edelman . |
| 4,465,463 | 8/1984 | Hson Olde . |
| 4,553,942 | 11/1985 | Sutter . |
| 4,600,388 | 7/1986 | Linkow . |
| 4,722,688 | 2/1988 | Lonca . |
| 4,856,648 | 8/1989 | Krueger . |
| 4,856,994 | 8/1989 | Lazzara et al. . |
| 4,955,811 | 9/1990 | Lazzara et al. . |
| 5,030,096 | 7/1991 | Hurson et al. . |
| 5,062,800 * | 11/1991 | Niznick ................. 296/368 |
| 5,100,323 | 3/1992 | Friedman et al. . |
| 5,105,690 | 4/1992 | Lazzara et al. . |
| 5,108,288 | 4/1992 | Perry . |
| 5,158,458 | 10/1992 | Perry . |
| 5,213,500 | 5/1993 | Salazar et al. . |
| 5,254,005 | 10/1993 | Zuest . |
| 5,290,171 | 3/1994 | Daftary et al. . |
| 5,297,561 * | 3/1994 | Hulon .................. 215/DIG. 3 |
| 5,302,125 | 4/1994 | Kownacki et al. . |
| 5,306,309 | 4/1994 | Wagner et al. . |
| 5,312,254 | 5/1994 | Rosenlicht . |
| 5,322,443 | 6/1994 | Beaty . |
| 5,368,160 * | 11/1994 | Leuschen et al. .......... 433/174 |

(List continued on next page.)

FOREIGN PATENT DOCUMENTS

| | | |
|---|---|---|
| 90 14 729 | 1/1991 | (DE) . |
| WO 96/25895 | 8/1996 | (WO) . |
| WO 98/52490 | 11/1998 | (WO) . |
| WO 98/53755 | 12/1998 | (WO) . |

*Primary Examiner*—Todd E. Manahan
(74) *Attorney, Agent, or Firm*—Knobbe, Martens Olson and Bear, LLP

(57) ABSTRACT

A carrier for a dental implant package to reliably and releasably hold a dental implant and to cap a packaging vial. The carrier includes a plurality of vial-engaging flexible fingers and a plurality of screw-engaging flexible fingers. The vial-engaging fingers engage a groove of the packaging vial to form a releasable mechanical lock. For cylindrical implants, the screw-engaging fingers grip a healing screw coupled to the cylindrical implant. The cylindrical implant carrier also includes a protrusion in the center to stabilize the cylindrical implant during transportation. For threaded implants, the screw-engaging fingers releasably engage a groove of an insertion tool screw coupled to the threaded implant. Advantageously, the carrier of the present invention provides a reliable long-term hold on a dental implant and a simple but effective removable cap for a packaging vial for the implant.

72 Claims, 10 Drawing Sheets

U.S. PATENT DOCUMENTS

| | | |
|---|---|---|
| 5,417,570 | 5/1995 | Zuest et al. . |
| 5,433,330 * | 7/1995 | Yatsko et al. .................... 215/DIG. 3 |
| 5,437,550 | 8/1995 | Beaty et al. . |
| 5,453,010 | 9/1995 | Klein . |
| 5,462,436 | 10/1995 | Beaty . |
| 5,507,643 | 4/1996 | Klein . |
| 5,525,314 | 6/1996 | Hurson . |
| 5,538,428 | 7/1996 | Staubli . |
| 5,558,230 * | 9/1996 | Fischer et al. ...................... 433/174 |
| 5,569,037 | 10/1996 | Moy et al. . |
| 5,582,299 * | 12/1996 | Lazzara et al. ...................... 206/438 |
| 5,622,500 | 4/1997 | Niznick . |
| 5,636,991 * | 6/1997 | Mays .................................... 206/368 |
| 5,683,464 | 11/1997 | Wagner et al. . |
| 5,692,904 | 12/1997 | Beaty et al. . |
| 5,755,575 * | 5/1998 | Biggs .................................... 433/173 |
| 5,887,707 | 3/1999 | Anascavage et al. . |
| 5,904,483 | 5/1999 | Wade . |
| 5,961,330 * | 10/1999 | Harison ................................ 433/173 |
| 5,964,591 | 10/1999 | Beaty et al. . |
| 5,967,305 | 10/1999 | Blonder et al. . |

* cited by examiner

COMBINATION IMPLANT CARRIER AND VIAL CAP

This application is a continuation-in-part of U.S. application No. 09/227,069 filed Jan. 5, 1999, and claims priority to Provisional Application No. 60/092,649 filed Jul. 13, 1998 and Provisional Application No. 60/092,674 filed Jul. 13, 1998, under 35 U.S.C. § 119 (e).

BACKGROUND OF THE INVENTION

1. Field of the Invention

The present invention relates generally to dental implants and, in particular, to a dental implant carrier with resilient fingers for reliably and releasably holding a dental implant and for interfacing with a packaging vial.

2. Background of the Related Art

Dental implants are surgically implanted in a patient's jawbone to provide anchors for prosthetic devices such as artificial teeth, crowns, bridges, dentures and the like. Dental implants allow people who lose their teeth to be able to smile, speak, and chew well and comfortably.

Typically, the dental implant that is implanted in the bone of a patient's jawbone supports a socket. This socket is accessible through the overlying gum tissue for receiving and supporting one or more dental attachments or components, such as healing screws, impression copings and abutments, among others. In turn, some of these components are useful to fabricate and/or to support the prosthodontic restoration.

Dental implant assemblies are generally packaged in a sterile environment and include the implant, an implant carrier and a healing screw. The carrier is used to hold the implant within a vial and during transport to a surgical site, and can also serve as a cap for the vial. Since the dental implant package is usually sterilized, the carrier allows the dental implant to be transported with minimal risk of contamination due to contact with the operator. The carrier also permits the implant to be inserted in a hole, osteotomy or alveolar cavity in the jawbone of a patient. In many cases, the dental implant assembly of the implant, carrier and healing screw is commercialized with the healing screw threadably engaged with the implant socket and the carrier engaged with the healing screw.

Such a commercialized dental implant assembly is typically used in conjunction with non-threaded or "cylindrical implants." Cylindrical implants comprise a non-threaded and generally smooth body portion which is simply pressfitted into the osteotomy. The other popular type of implant is usually referred to as a "threaded implant" and comprises a threaded body portion which is screwed into the osteotomy. The choice of implant is usually dictated by the particular bone structure surrounding the osteotomy and in many instances on the particular personal preference of the dentist or periodontist. A typical commercialized dental implant assembly with a threaded implant may include one or more additional components such as an insertion tool/post and an insertion tool screw for facilitating in the transfer and seating of the threaded implant and healing screw.

In use, the first step usually involves making an incision in the patient's gum. Next, typically, a hole or osteotomy is drilled in the jawbone of the patient and the implant is fixtured into the osteotomy. The carrier is used to transport the implant to the surgical site and to seat the implant in its proper subgingival position. For cylindrical implants, the carrier is removed from the assembly leaving the healing screw threadably coupled to the cylindrical implant in the osteotomy. For threaded implants, the carrier is then pulled from the insertion tool screw. The insertion tool screw is removed from the threaded implant and the healing screw is threaded into the socket of the threaded implant. The healing screw prevents the ingrowth of bone inside the implant.

This is followed by a healing period in which the bone is allowed to grow and surround and retain the implant (or to osseointegrate with the implant) and the gum tissue is allowed to heal over the implant and the healing screw. For implants in the mandible, healing typically requires about three months; for implants in the maxilla, the healing period is usually about six months. The healing screw protects the implant socket against bone/tissue ingrowth during this healing period, and also prevents the entry of bacteria or other contaminants into the exposed central socket/bore of the implant.

After the osseointegration occurs and the gun has healed, the gum is reopened by making an incision in it and the healing screw is removed. A suitable healing abutment is attached to the implant. A second healing period ensues in which the gum tissue is allowed to heal around the healing abutment Typically, this second healing period lasts from four to eight weeks.

After the second healing period, the healing abutment is removed from the implant. Typically, an impression is taken of the patient's mouth to fabricate a prosthesis or dental restoration. An abutment which supports the final restoration is attached to the implant. Lastly, the restoration is cemented or screwed to the abutment and/or implant to complete the placement of the prosthodontic restoration in the patient's mouth.

Referring in particular to cylindrical dental implant assemblies, there are several potential problems associated with conventional cylindrical implant carriers. Conventional carriers generally include a cap at one end for manual gripping and a protrusion or nipple at the other end. The protrusion engages a cavity in the head of the healing screw and provides an interference fit between the carrier protrusion and the healing screw cavity. Since the healing screw is threaded into the implant socket, the implant is thereby held via the carrier and healing screw engagement. The carrier is bent relative to the head of the screw and/or pulled, to remove it from the healing screw. Such a cylindrical implant carrier is described in U.S. Pat. No. 5,030,096, incorporated herein by reference.

The holding mechanism as incorporated by the above-mentioned interference fit has demonstrated a low frequency of failure. It is not uncommon for commercialized dental implant assemblies to be transported by common carrier and be exposed to temperature variations and vibrations. This can result in disengagement of the carrier and the implant during shipping. Moreover, a dental implant assembly may be subject to similar adverse temperature variations and vibrations while it is on-the-shelf or in storage. In many cases, this on-the-shelf and storage period may span over a period of several years. Hence, the quality of the interference fit between the cylindrical implant carrier and the healing screw may degrade over time. It is especially inconvenient if the dental implant slips out of the carrier during a dental procedure. Also, the interference friction fit between the carrier protrusion and the healing screw cavity provides poor manufacturing repeatability and, therefore, can undesirably result in either insufficient or considerably large holding forces between the cylindrical implant carrier and the healing screw.

Additionally, the removal mechanism of the carrier from the healing screw can result in breakage of the carrier protrusion, since this removal involves bending of the carrier relative to the head of the healing screw. The torque generated during such bending may be sufficiently high to cause breakage or fracture of the protrusion from the carrier, especially since the protrusion is forming a frictional interference fit with the healing screw cavity. Again, this is inconvenient during a dental procedure.

One popular technique of packaging the commercialized dental implant assembly utilizes an extrusion or annular ring. The extrusion is fabricated from a resilient material and slides onto a medial portion of the carrier adjacent to the cap of the carrier. Thus when the dental implant is packaged in the vial the extrusion serves to provide an interference fit with the wall of the vial while the carrier cap serves as a cap for the package.

Disadvantageously, this frictional interference fit between the extrusion and the vial has demonstrated a low frequency of failure for reasons similar to those discussed above. These being exposure to shock and temperature variations during shipping and handling, and even possibly during on-the-shelf and storage periods. Additionally, the interference friction fit provides poor manufacturing repeatability and, therefore, can result in either insufficient or considerably large retaining forces between the carrier and the vial.

Moreover, and undesirably, the fabrication of the extrusion requires the manufacture of an additional component for the dental implant packaging and increases the number of components comprising the dental implant packaging. Also, the assembly of the packaging requires the additional step of sliding the extrusion over the carrier. All this disadvantageously adds to the cost of the dental implant packaging.

Therefore, it would be desirable to provide a dental implant packaging that can reliably and effectively hold a dental implant over a substantially prolonged period of time while being generally unaffected by ambient inclement conditions. There is also a need to provide a dental implant packaging for reliably and releasably fixturing a dental implant assembly in a packaging vial while concurrently maintaining simplicity in design and low cost.

SUMMARY OF THE INVENTION

The present invention overcomes some or all of the above-mentioned disadvantages by providing a dental implant carrier with a screw-engaging set of fingers and a vial-interfacing set of fingers. Preferably, the screw-engaging set of fingers is adapted to reliably and releasably grip a dental screw coupled to an implant In the case of cylindrical implants, the dental screw held by the carrier is a healing screw for capping the cylindrical implant in an osteotomy. For threaded implants, the dental screw held by the carrier is an insertion tool screw which, along with an insertion tool, facilitates the insertion of the threaded implant in an osteotomy. Preferably, the vial-interfacing set of fingers is adapted to interface with a packaging vial so that a dental implant assembly, including the implant, the dental screw, the carrier (and the insertion tool, in the case of threaded implants), is releasably held in the vial and a removable cap is provided for the packaging vial.

Advantageously, the vial-interfacing fingers are flexible and resiliently displaceable and include respective projecting portions for releasably mechanically locking into a groove formed on an inner surface of the vial. It is generally preferred that the vial-interfacing fingers lock or latch into the vial groove while creating a minimal amount of interference fit between the vial-interfacing fingers and the vial. Desirably, this allows the carrier to be removed from the vial by applying a predictable and low level of force while concurrently permitting a reliable interfacement between the carrier and the vial. Incorporating such a vial interfacing mechanism in the carrier structure advantageously eliminates the need for the fabrication of an extra vial interfacing component as is conventionally done. This simplifies the packaging of the commercialized dental implant and, desirably, reduces the cost. Moreover, the vial-interfacing finger projecting portions provide a desirable camming action during removal (and insertion) of the dental implant assembly from (into) the vial which assists the user.

Advantageously, the healing screw-engaging fingers of the cylindrical implant carrier are flexible and resiliently displaceable, and are sized and configured to form an interference fit over the periphery of the healing screw head. Additionally, a generally central shaft or protrusion is provided to engage a wrench-receiving cavity in the head of the healing screw to stabilize the grip of the screw-engaging fingers on the head of the screw. Such a gripping mechanism substantially overcomes or reduces the above-mentioned problem of the cylindrical implant becoming detached from the carrier during inclement ambient conditions, such as vibrations and temperature variations particularly during shipping and handling. Moreover, during removal of the cylindrical implant carrier from the healing screw, the screw-engaging fingers are generally flexed and slide over the head of the healing screw, thereby substantially overcoming or reducing the chance of their breakage.

Advantageously, the insertion tool screw-interfacing fingers of the threaded implant carrier are flexible and resiliently displaceable and include respective projecting portions for releasably mechanically locking into a groove formed on the insertion tool screw. The screw-interfacing fingers can also be dimensioned and configured to apply a generally radial compressive force (interference fit) on the insertion tool screw. Desirably, the insertion tool screw engaging fingers provide a reliable and releasable hold on the insertion tool screw, and hence the threaded implant. Moreover, the screw-interfacing finger projecting portions provide a desirable camming action during removal (and insertion) of the insertion tool screw from (into) the threaded implant carrier which assists the user.

For purposes of summarizing the invention and the advantages achieved over the prior art, certain objects and advantages of the invention have been described herein above. Of course, it is to be understood that not necessarily all such objects or advantages may be achieved in accordance with any particular embodiment of the invention. Thus, for example, those skilled in the art will recognize that the invention may be embodied or carried out in a manner that achieves or optimizes one advantage or group of advantages as taught herein without necessarily achieving other objects or advantages as may be taught or suggested herein.

All of these embodiments are intended to be within the scope of the invention herein disclosed. These and other embodiments of the present invention will become readily apparent to those skilled in the art from the following detailed description of the preferred embodiments having reference to the attached figures, the invention not being limited to any particular preferred embodiment(s) disclosed.

DETAILED DESCRIPTION OF THE PREFERRED EMBODIMENTS

Cylindrical Implant Carrier

Figure 1:
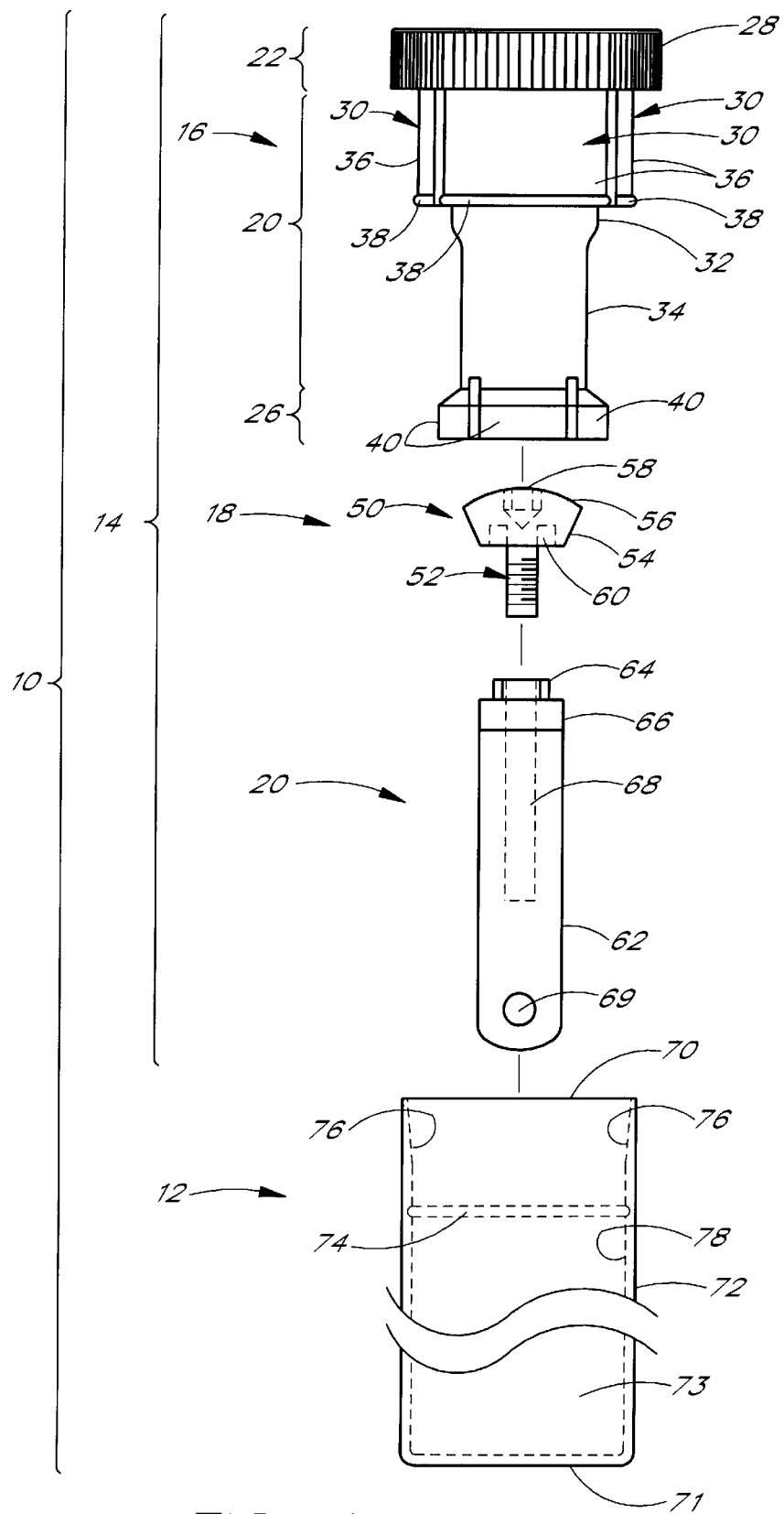
FIG. 1 is an exploded side elevational view of a dental implant package including a cylindrical implant carrier in accordance with one preferred embodiment of the present invention.
Figure 5:
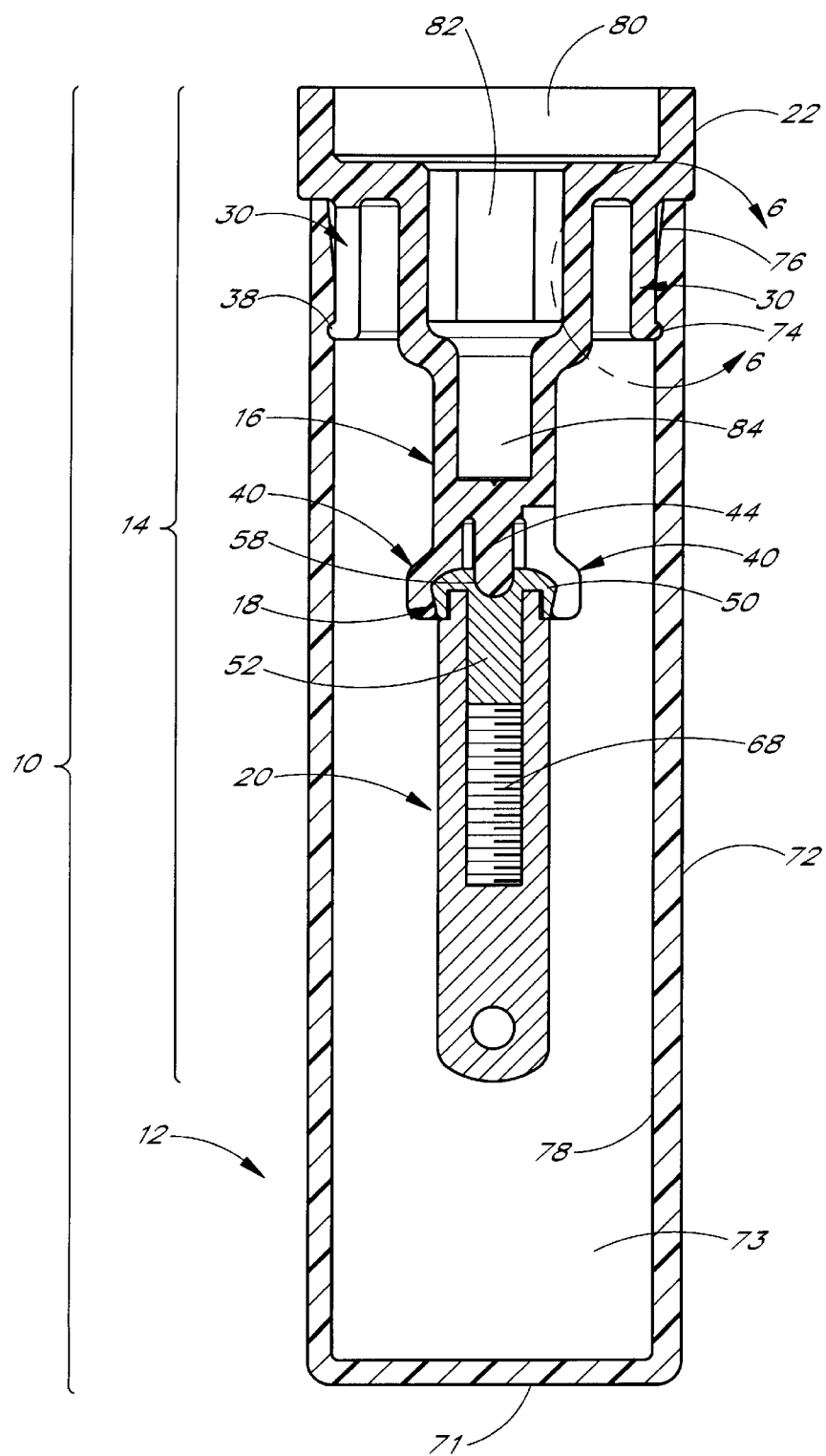
FIG. 5 is a cross-sectional view illustrating the engagement of the carrier with the vial and healing screw of FIG. 1.

Referring particularly to FIGS. 1 and 5, one preferred embodiment of a dental implant package/combination 10 constructed and assembled in accordance with the present invention includes a vial 12 and a dental implant assembly/kit 14 comprising a cylindrical implant carrier 16, a healing screw 18 and a cylindrical dental implant 20. The carrier 16 reliably and releasably grips the screw 18 and serves as a handle or holder for transporting the implant 20 and healing screw 18 to a surgical site and facilitates insertion of the implant 20 into an osteotomy or alveolar cavity in the jawbone of a patient. The carrier 16 also reliably and releasably interfaces with the vial 12 to provide a detachable cap for the vial 12.

Figure 2:
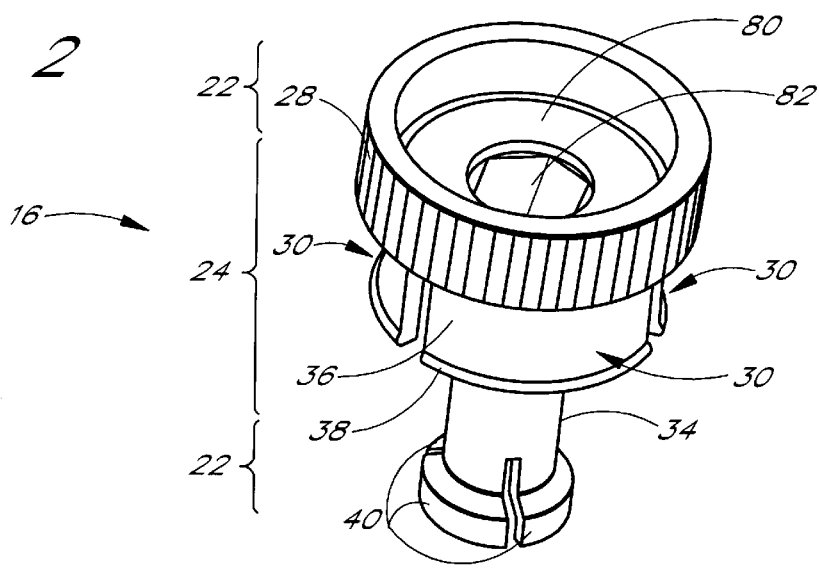
FIG. 2 is a perspective view of the carrier of FIG. 1.
Figure 3:
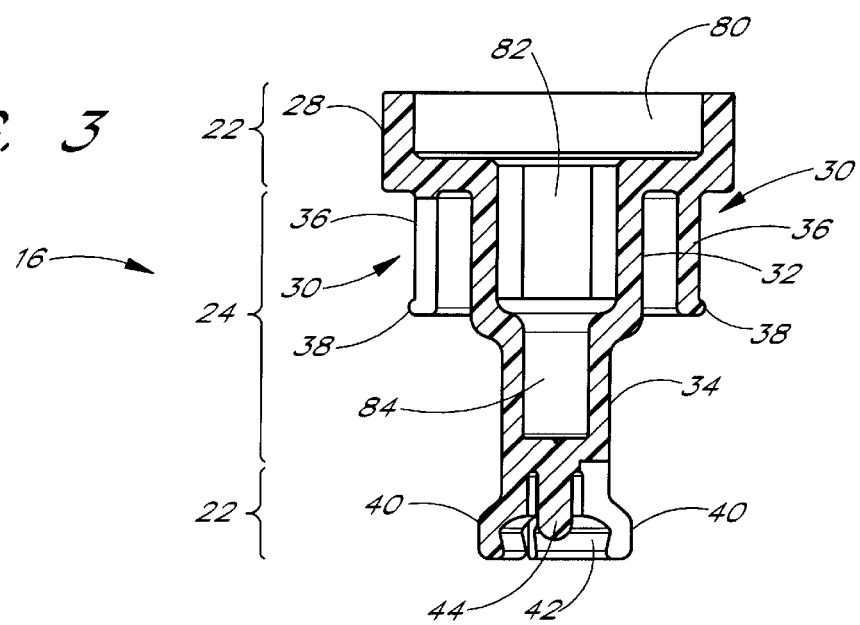
FIG. 3 is a cross-sectional detail view of the carrier of FIG. 1.

Preferably, and as can be seen in FIGS. 1 to 3, the implant carrier 16 comprises an anterior section/cap 22, a medial section 24 and a posterior section 26. The anterior section/cap 22 is preferably generally cylindrical in shape and has a substantially central cylindrical cavity 80. Optionally, the outer curved surface 28 of the anterior section 22 may be ridged, grooved or knurled to provide a convenient gripping surface.

Referring in particular to FIGS. 1 to 3, preferably, the carrier medial section 24 includes a plurality of vial-engaging fingers 30, and a pair of generally cylindrical first and second spacing members or shafts 32 and 34. The spacing members 32, 34 generally serve the function of spacing the carrier anterior section/cap 22 and the carrier posterior section 26. The fingers 30 are in communication with and extend away from the carrier anterior section/cap 22 towards the carrier posterior section 26. The fingers 30 are spaced from and generally circumscribe the first spacing member 32. The medial section first spacing member 32 is in communication with the carrier anterior section 22 and includes a generally hexagonal cavity 82 (FIGS. 2 and 3) which is in communication with the carrier anterior section cavity 80. This hexagonal cavity 82 facilitates the assembly of the dental implant assembly/kit 14, as discussed later herein. The medial section second spacing member 34 is in communication with the carrier posterior section 26 and includes a generally cylindrical cavity 84 which is in communication with the hexagonal cavity 82.

Preferably, and referring in particular to FIGS. 1 to 3, the fingers 30 are flexible, and hence resiliently displaceable relative to the medial section first spacing member 32. In one preferred form of the present invention, the plurality of fingers 30 comprises three fingers FIGS. 1 and 2). But as will be readily apparent to those of ordinary skill in the art, more or fewer fingers may be utilized with efficacy, as needed or desired, giving due consideration to the desired goal of providing a reliable and releasable interface with the vial 12 (FIGS. 1 and 5). It is generally preferred to have three to six vial-interfacing fingers 30. Preferably, the fingers 30 are arranged in a substantially symmetrical fashion and substantially equidistantly spaced from their respective neighboring fingers. Of course, the fingers 30 may be alternatively spaced in a variety of configurations or patterns with efficacy, giving due consideration to the goal of providing a reliable and releasable interface with the vial 12 (FIGS. 1 and 5). In one preferred embodiment of the present invention, the fingers 30 are integrally molded with the carrier 16.

Referring in particular to FIGS. 1 to 3, preferably, each one of the fingers 30 has a respective body portion 36 and a respective bottom projecting or bulging end 38. The finger body portions 36 are preferably spaced from the first spacing member 32 to create clearance space for the resilient displacement of the fingers 30. The finger body portions 36 are curved to generally follow the curvature of the first spacing member 32 and the vial 12 (FIGS. 1 and 5) with which the carrier 16 mates.

Preferably, and referring in particular to FIGS. 1 to 3, the bottom ends 38 of the respective fingers 30 project or bulge generally radially outwards relative to the first spacing member 32, and are generally thicker than the respective finger body portions 36. The finger bottom ends 38 are preferably spaced from the first spacing member 32 to create clearance space for the resilient displacement of the fingers 30. Preferably, the finger bottom ends 38 are curved to generally follow the curvature of the medial section first spacing member 32 and the vial 12 (FIGS. 1 and 5) with which the carrier 16 mates. The projection or bulging of the finger bottom ends 38 serves to form a detent mechanism for relative engagement with mating inner surfaces of a cylindrical vial. In particular, and as will be discussed in more detail later herein, the bulging or projecting of the finger bottom ends 38 cooperates with an annular or circumferential groove formed on the vial 12 (FIG. 1) to lock the carrier 16 into the vial 12.

Figure 4:
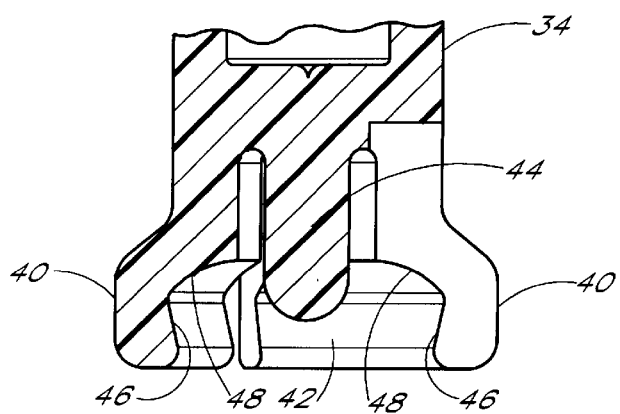
FIG. 4 is an enlarged view of the carrier's healing screw gripping fingers as shown in FIG. 3.

Referring in particular to FIGS. 1 to 4, preferably, the carrier posterior section 26 includes a plurality of screw-engaging fingers 40 which generally enclose a cavity 42 with a central shaft or protrusion or nipple 44 (FIGS. 3 and 4). The fingers 40 are in communication with and extend away from the second spacing member 34 of the carrier medial section 24. Preferably, the fingers 40 are flexible, and hence resiliently displaceable relative to the medial section second spacing member 34. In one preferred form of the present invention, the plurality of fingers 40 comprises three fingers (FIGS. 1 and 2). But as will be readily apparent to those of ordinary skill in the art, more or fewer fingers may be utilized with efficacy, as needed or desired, giving due consideration to the desired goal of providing a reliable and releasable grip on the healing screw 18 (FIGS. 1 and 5). It is generally preferred to have three to six screw-engaging fingers 40. Preferably, the fingers 40 are arranged in a substantially symmetrical fashion and substantially equidistantly spaced from their respective neighboring fingers. Of course, the fingers 30 may be alternatively spaced, with efficacy, giving due consideration to the goal of providing a reliable and releasable grip on the healing screw 18 (FIGS. 1 and 5). In one preferred embodiment of the present invention, the fingers 40 are integrally molded with the carrier 16.

Referring to FIGS. 1 to 4, the screw-engaging fingers 40 are configured and sized to capture the head of a healing screw, such as the healing screw 18 (FIGS. 1 and 5). Thus, the particular construction of the fingers 40 is dependent on the configuration and dimensioning of the healing screw 18. Though the drawings illustrate a specific configuration of the fingers 40, it is to be understood that the fingers 40 may be alternately configured and dimensioned with efficacy, as required or desired, giving due consideration to the desired goals of providing a releasable and reliable grip on a healing screw. In one preferred embodiment of the present invention, and as best seen in FIG. 4, the fingers 40 include an inner tapered surface 46 and an inner curved surface 48, and protrude generally outwards relative to the carrier second spacing member 34. Again, this configuration is adapted to conform with the configuration of the healing screw 18 (FIGS. 1 and 5). The shaft or protrusion 44 is configured and dimensioned to engage a cavity of the healing screw 18, as discussed below.

The healing screw 18 (FIGS. 1 and 5) comprises a head 50, which is gripped by the carrier fingers 40, and a threaded portion 52 to threadably engage the implant 20. The head 50 includes a tapered wall 54 and a curved crown/roof 56 with a cavity 58. The cavity 58 is generally hexagonal in shape and is adapted to receive a suitable insertable wrench to screw or unscrew the healing screw 18. The cavity 58 is also configured to receive the carrier protrusion or shaft 44 FIGS. 3 to 5), thereby providing further stability to the hold of the carrier 16 on the healing screw 18. Preferably, the carrier shaft 44 forms a slip fit in the healing screw cavity 58. Optionally, the carrier shaft 44 may form an interference friction fit in the healing screw cavity 5, giving due consideration to the goal of providing stability to the grip of the carrier fingers 40 on the healing screw head 50. The healing screw head 50 may also include a generally annular cavity 60 to facilitate attachment to an implant, such as the implant 20, having a raised hex interlocking post.

While the present invention may be used with a wide variety of dental implants, a very satisfactory and widely used cylindrical dental implant 20 is shown in FIGS. 1 and 5. The implant 20 includes a body or root portion 62, a generally hexagonal post 64 at the exposed top end 66, and a threaded socket 68 originating from the exposed end 66 and into the body portion 62. The implant body portion 62 is generally cylindrical and generally smooth, and is adapted to engage an osteotomy or alveolar cavity in the jawbone of a patient. As is known in the art, the hexagonal post 64 is configured to substantially irrotationally mate with a hexagonal cavity of an abutment (not shown) on which the final prosthesis (not shown) is mounted. The healing screw cavity 60 provides clearance for the implant post 64 when the screw threaded portion 52 threadably engages the implant threaded socket 68 to attach the healing screw 18 to the dental implant 20. The implant body portion 62 may include a passage 69 formed therethrough to permit in-growth of bone and tissue for locking or anchoring the implant in the osteotomy following installation.

Figure 6:
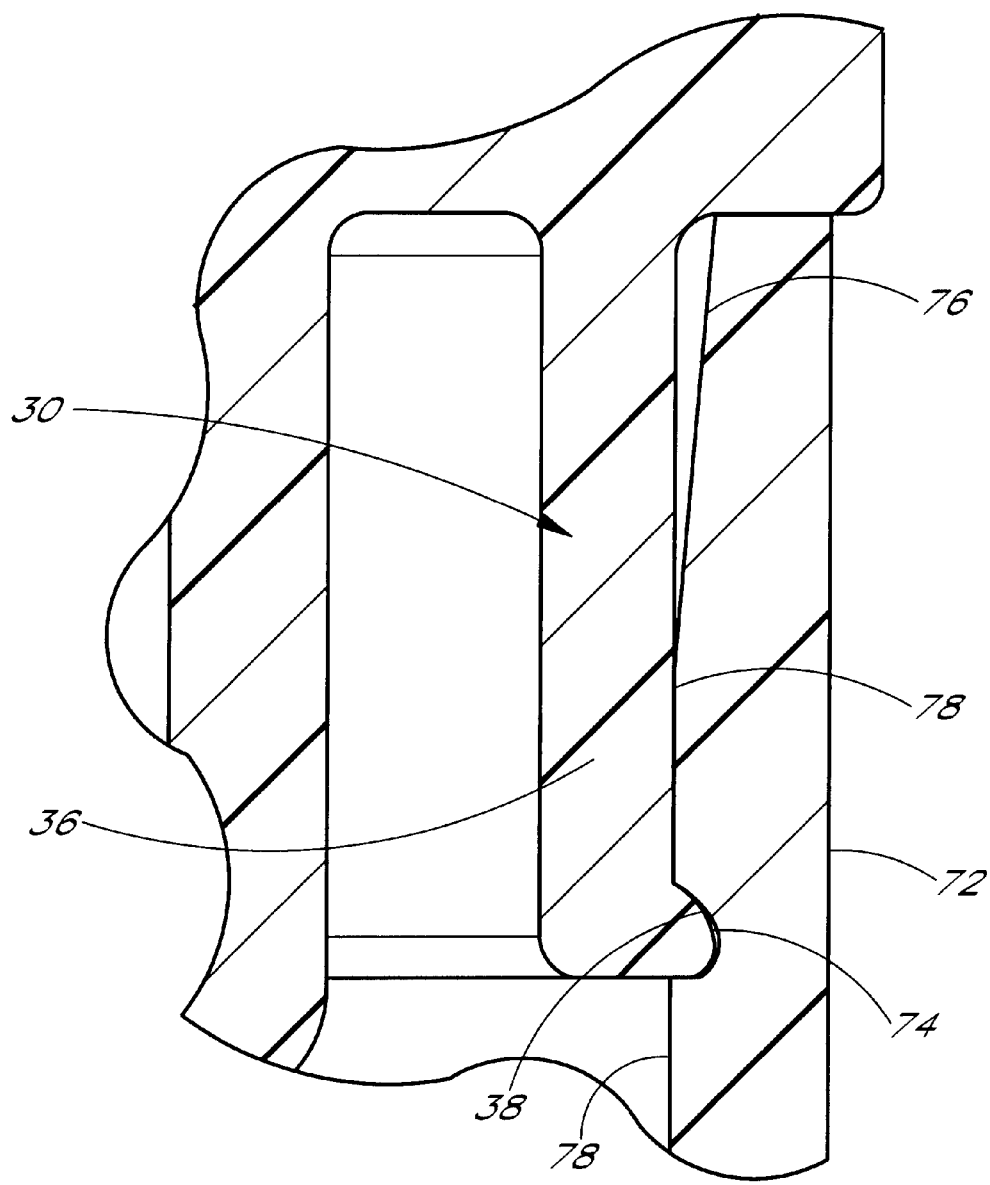
FIG. 6 is an enlarged view of the carrier's vial engaging fingers as shown in FIG. 5.

Referring to FIGS. 1 and 5, the packaging vial 12 preferably comprises an open end 70, a closed end 71 and a generally cylindrical side wall 72 to form a hollow cavity 73 to receive the dental implant assembly/kit 14. Preferably, the side wall 72 includes a tapered inner surface 76 (FIGS. 5 and 6) proximate to the open end 70 culminating in an inner surface 78 (FIGS. 5 and 6) with a generally circumferential or annular groove or notch 74. The groove 74 is preferably spaced from the tapered inner surface 76. The tapered surface 76 facilitates the insertion and removal of the flexible fingers 30 through the vial open end 70. As best seen in FIG. 6, the groove 74 is configured and positioned to receive the projecting or bulging bottom ends 38 of the fingers 30 to provide a mechanical lock between the carrier 16 and the vial 12. Though the projecting or bulging finger bottom ends 38 (FIG. 6) are shown in the drawings as being generally bulbous and the vial groove 74 to be generally circumferential and annular, alternate configurations may be employed with equal efficacy, giving due consideration to the goals of providing a reliable and releasable lock between the implant carrier 16 and the vial 12. For example, other recesses, either continuous or discrete, may be formed on the vial inner surface 78 (FIGS. 5 and 6) to provide a locking niche for the carrier fingers 30. In the assembled state of the dental implant package 10 (FIG. 5), the carrier anterior section/cap 22 serves as a removable cap for the vial 12, thus providing a container for the healing screw 18 and dental implant 20.

The implant carrier 16, shown, for example, in FIGS. 1, 2 and 3, is preferably fabricated from a thermoplastic material, though other suitable plastics, rubbers, metals, alloys and ceramics may be utilized with efficacy, giving due consideration to the goals of providing reliable and releasable attachment to the carrier 16. In one preferred form of the invention, the implant carrier 16 is fabricated from a nylon such as 25% glass-reinforced nylon or ultramid B3WG5 nylon 6. Alternatively, the carrier fingers 30 and/or 40 may be fabricated from a material different than the rest of the carrier 16, as needed or desired, giving due consideration to the goals of providing reliable and releasable attachment to the carrier 16.

Preferably, and referring, for example, to FIG. 1, the healing screw 18 and the dental implant 20 are fabricated from pure titanium or a titanium alloy, which are compatible with bone, fixtures, tools, and the ultimate prosthesis, as well as being innocuous in use over time. Of course, the healing screw 18 and the implant 20 may be fabricated from or coated with other suitable metals, alloys, allographic materials, liquid crystal polymers (LCP) and ceramics, as required or desired, giving due consideration to the goals of providing bio-compatibility, inertness, corrosion-resistance and durability. The vial 12 (FIGS. 1 and 5) is, preferably, fabricated from a light-weight, durable, clear plastic, though other materials may be used with equal efficacy, giving due consideration to the goals of providing reliable and releasable attachment to the carrier 16.

In one form of the present invention the carrier 16, shown for example in FIGS. 2 and 3, has an overall length of about 0.710 inches and a maximum diameter between about 0.510 inches and about 0.530 inches. The vial-engaging fingers 30 have a length of about 0.189 inches and are arranged so that their respective body portions 36 form an outer diameter of about 0.427 inches. The screw-engaging fingers 40 are about 0.135 inches long and are arranged so that the screw-head engaging cavity 42 (FIGS. 3 and 4) has a maximum diameter in the range of about 0.128 to 0.212 inches to accommodate a range of screw head 50 (FIG. 1) sizes. The inner tapered surfaces 46 (FIG. 4) of the fingers 40 have a taper angle of about 5° to about 15°, and again this is to accommodate a range of types of screw heads 50 (FIG. 1). Those skilled in the art will readily recognize that the carrier 16 of the present invention may be sized and dimensioned in alternate ways with equal efficacy, giving due consideration to the goals of providing reliable and releasable attachment to the carrier 16.

Figure 7A:
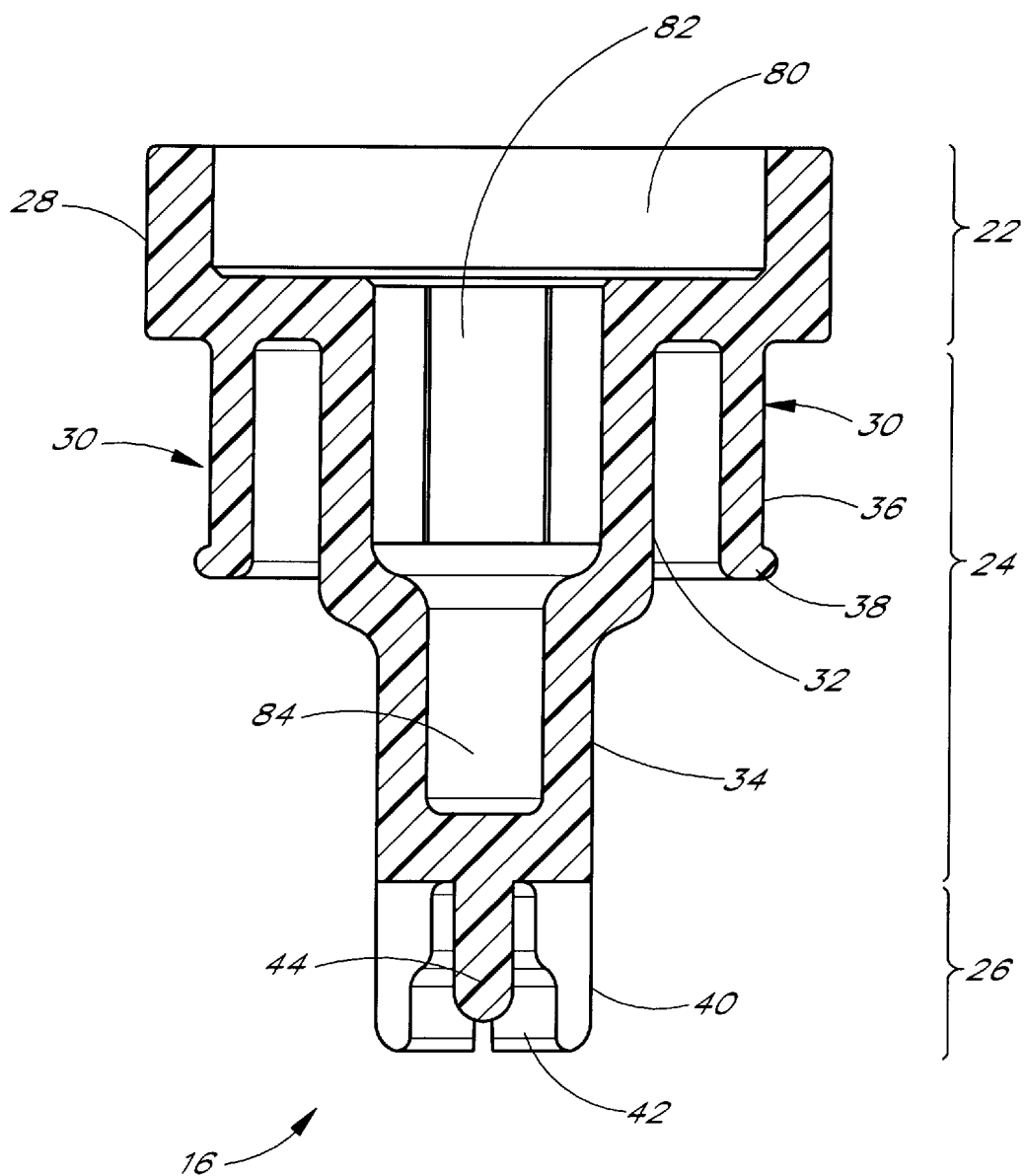
FIG. 7A is a cross-sectional detail view illustrating a cylindrical implant carrier in accordance with one embodiment of the present invention.
Figure 7B:
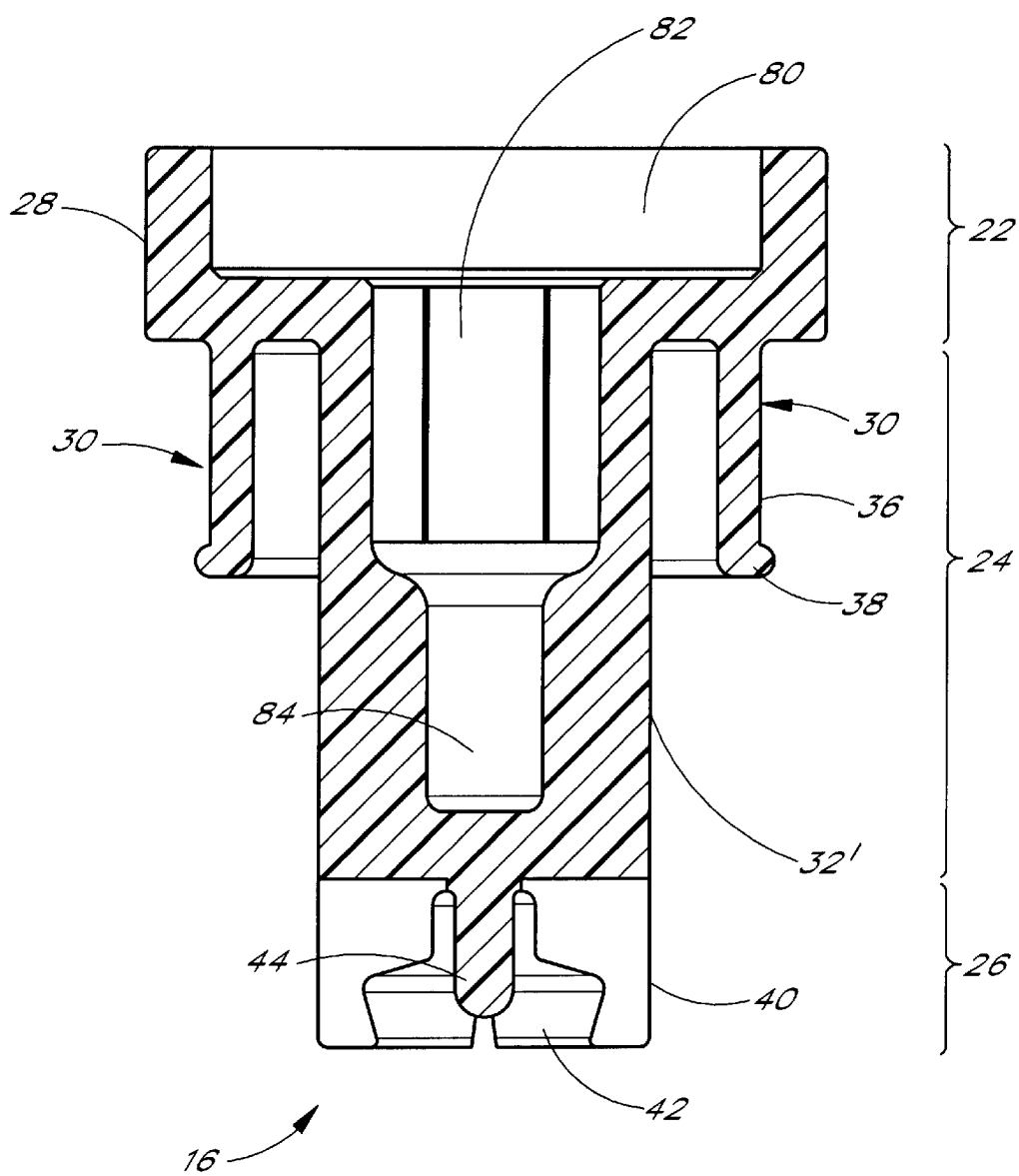
FIG. 7B is a cross-sectional detail view illustrating a cylindrical implant carrier in accordance with another embodiment of the present invention.
Figure 7C:
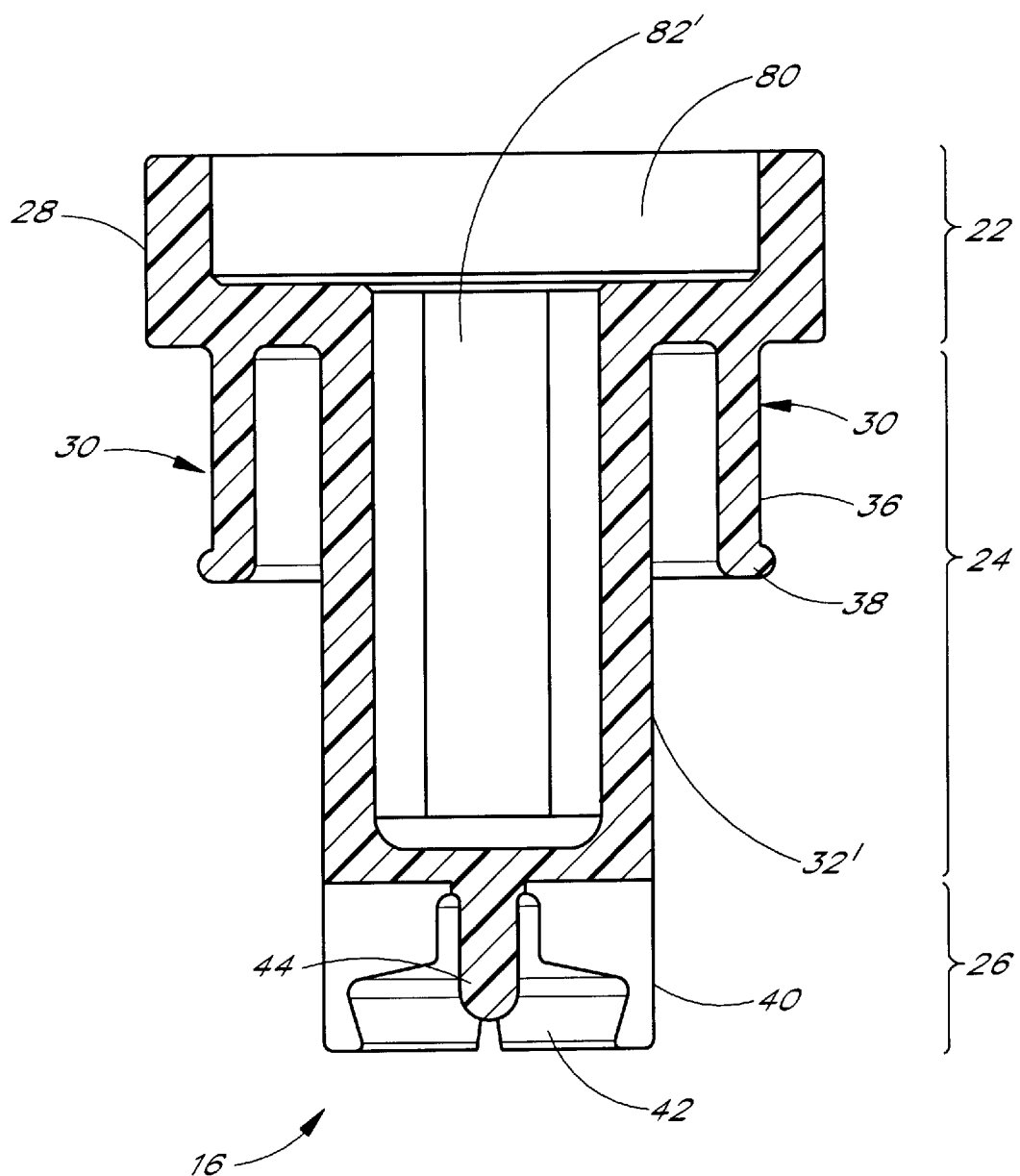
FIG. 7C is a cross-sectional detail view illustrating a cylindrical implant carrier in accordance with yet another embodiment of the present invention.

The carrier 16 of the present invention may also be configured in other preferred ways. Referring to FIGS. 7A to 7C, the carrier 16 may be constructed so that the fingers 40 do not protrude outwards with respect to the spacing member 34 (FIG. 7A), 32' (FIGS. 7B and 7C) with which they are in communication. Such a construction can be well suited for injection molding manufacture of the carrier 16. Alternatively, the medial section 24 may include only one spacing member 32' (FIGS. 7B and 7C) and a generally hexagonal cavity 82' (FIG. 7C) traversing about the entire length of the medial section 24, as desired.

Advantageously, the cylindrical implant carrier 16 of the present invention provides several benefits and advantages over conventional carriers by incorporating flexible fingers 30 and 40 to interface with the vial 12 and the healing screw 18, respectively. The screw-gripping fingers 40 provide a predictable interference fit over the periphery of the head 50 of the healing screw 18. During insertion of the healing screw 18 into the cavity between the fingers 40, the fingers 40 are flexed outwards as the finger tapered surfaces 46 (FIG. 4) slide over the screw tapered wall 54 (FIG. 1) until the curved screw crown/roof 56 (FIG. 1) contacts or is close to the finger curved surfaces 48 (FIG. 1). This gripping mechanism, advantageously, provides a reliable but releasable hold on the healing screw 18 by the carrier 16. The fingers 40, in addition to applying a generally radial compressive force on the screw head 50, also provide a latching between the screw head 50 and the fingers 40 due to the contact between the screw tapered wall 54 (FIG. 1) and the finger inner tapered surfaces 46 (FIG. 4). This also results in a desirable camming action during the attachment of the healing screw 18 to the carrier 16. In one preferred form of the invention, the interference fit between the screw head 50 and the fingers 40 is between about 4% to about 9%. Of course, the degree of this interference fit can be varied to suit the particular needs of the application, giving due consideration to providing a reliable and releasable grip between the fingers 40 and the screw 18. Desirably, the protrusion or shaft 44 is received in the screw cavity 58 and serves as a stabilizer against possible unwanted bending movement (similar to a ball and socket joint motion) between the carrier 16 and the healing screw 18. This can be especially important when the dental implant package 10 is subject to inclement ambient conditions, such as vibrations and shock during shipping and handling. As mentioned above, the carrier shaft 44 can also form an interference friction fit in the screw cavity 58 and, therefore, concurrently stabilize and enhance the grip of the fingers 40 on the healing screw 18.

Once the carrier 16 and healing screw 18 have been attached, the healing screw threaded portion 52 is screwed into the threaded socket 68 of the implant 20 to complete the assembly of the dental implant assembly/kit 14 (FIGS. 1 and 5). Preferably, this is accomplished by using a torque wrench (not shown) which engages the carrier hexagonal cavity 82 and hence tightens the healing screw to a predetermined torque level such that when the implant 20 is inserted in a patient's osteotomy the healing screw 18 does not require further tightening. In one form of the invention this torque level is about 3 inch-ounces. Preferably, the frictional grip of the fingers 40 on the screw head 50 is strong enough so that the fingers 40 will not rotatingly slide or slip over the screw head 50 during the tightening of the screw 18 to the implant 20.

Advantageously, the vial interfacing fingers 30 provide a reliable mechanical lock between the carrier 16 and the vial 12 with the finger projecting ends 38 (FIG. 6) engaging the vial groove 74 (FIG. 6). In this manner, the carrier 16 also provides a cap for the vial 12 with the carrier anterior/cap section 22 seated at the vial open end 70. During insertion of the carrier 16 in the vial cavity 73 (FIG. 5), the fingers 30 are flexed inwards as they slide over the tapered inner surface 76 (FIG. 6) of the vial side wall 72 (FIG. 6) and then over the flat inner surface 78 (FIG. 6). Advantageously, this tapering of the inner surface 76 facilitates in the insertion of the carrier 16 in the vial cavity 73. As best shown in FIGS. 5 and 6, the fingers 30 then flex outwards, preferably close to their unflexed state, as the finger projecting or bulging bottom ends 38 engage the vial groove or recess 74 to form a positive lock between the carrier 16 and vial 12. It is preferred that this engagement between the fingers 30 and the vial groove 74 provide a lock or latch with a minimal amount of interference fit. Advantageously, such an engagement creates a reliable fixturing between the carrier 16 and vial 12 which is concurrently releasable by applying a predictable and minimal level of force. This is convenient when the dental assembly/kit 14 (FIGS. 1 and 5) is removed from the vial 12. Additionally, since the "pre-stressing" or "deformation" of the fingers 30 in the assembled state is preferably minimal, it reduces the possibility of the fingers 30 losing their resilience during a long on-the-shelf and/or storage life. Desirably, the preferred generally bulbous shape of the finger projecting bottom ends 38 provides a camming action during insertion and removal of the carrier 16 in the vial cavity 73. Also, the degree of the interference fit between the carrier fingers 30 and the vial 12 can be increased or decreased, as required or desired, giving due consideration to the goals of providing a reliable fixturing between the carrier 16 and the vial 12 such that the carrier 16 is manually releasable from the vial 12 by applying a generally predictable low level of force.

In use, the dental implant assembly/kit 14 (FIGS. 1 and 5) is removed from the dental implant package 10 (FIGS. 1 and 5) by manually gripping the carrier anterior section/cap 22 and pulling it. During this removal, the vial-interfacing fingers 30 are released from their lock in the vial groove 74 (FIG. 6). The fingers 30 are initially flexed inwards as the finger projecting bottom ends 38 slide out of the vial groove 74 and over the part of the vial flat inner surface 78 between the vial groove 74 and the vial tapered inner surface 76. The fingers 30 then begin to flex in the opposite direction as the finger projecting bottom ends 38 slide over the vial tapered inner surface 76. As the finger projecting bottom ends 38 are extracted from the vial cavity 73 through the vial open end 70, the fingers 30 return to their generally unflexed state. Thus, the dental implant assembly/kit 14 is removed from the vial 12.

The dental implant assembly/kit 14 (FIGS. 1 and 5) is transported to a surgical site by holding the carrier anterior section/cap 22. At this stage, the carrier 16 is reliably and releasably gripping the healing screw 18 which in turn is attached to the dental implant 20. Since the fingers 40 reliably grip the screw head 50, the implant 20 is prevented from coming loose from the dental implant assembly/kit 14. While still manually holding the carrier anterior section/cap 22, the implant 20 is inserted in an osteotomy or alveolar cavity in the jawbone of a patient. The cylindrical implant 20 can simply be press-fitted into the osteotomy by utilizing the carrier 16 to push the implant 20 into the appropriate subgingival position in the osteotomy. The implant carrier 16 is then pulled and/or bent to one side to loosen and release the grip of the fingers 40 on the healing screw 18, thereby leaving the implant 20 in the osteotomy with the healing screw 18 capping the implant 20.

The cylindrical implant carrier 16 (FIGS. 1 to 3) may also be configured utilizing only one of the pair of sets of fingers 30 and 40. For example, the carrier 16 may be constructed with a plurality of vial-engaging fingers 30 to provide a cap for the vial 12 and employ a conventional attachment scheme to hold the healing screw 18. Alternatively, the carrier may be formed with a plurality of screw-gripping fingers 40 to grip the healing screw 18 and utilize a conventional engaging scheme to cap the vial 12.

Threaded Implant Carrier

Figure 8:
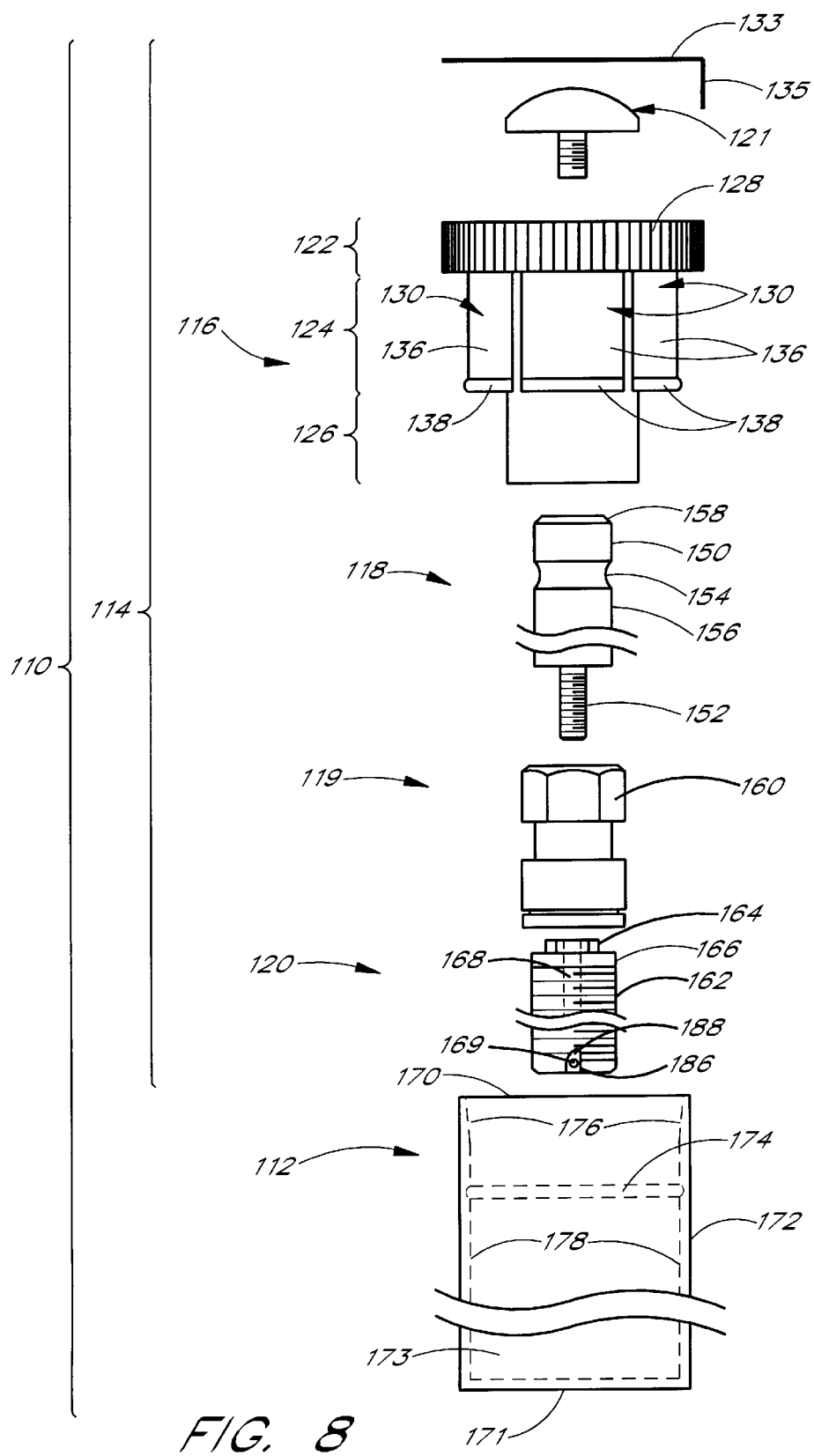
FIG. 8 is an exploded side elevational view of a dental implant package including a threaded implant carrier in accordance with one preferred embodiment of the present invention.
Figure 9:
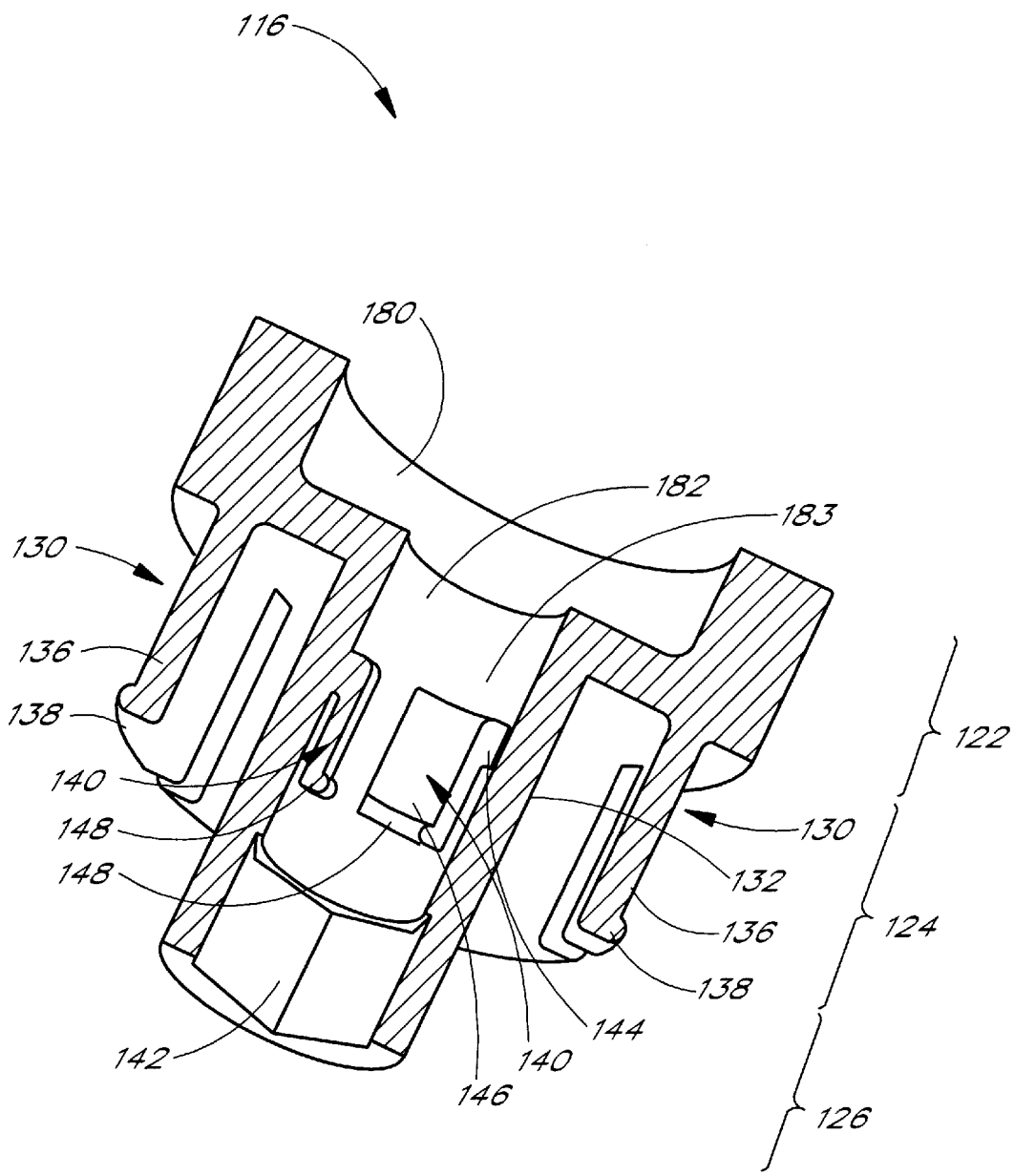
FIG. 9 is a cross-sectional detail view of the carrier of FIG. 8.
Figure 10:
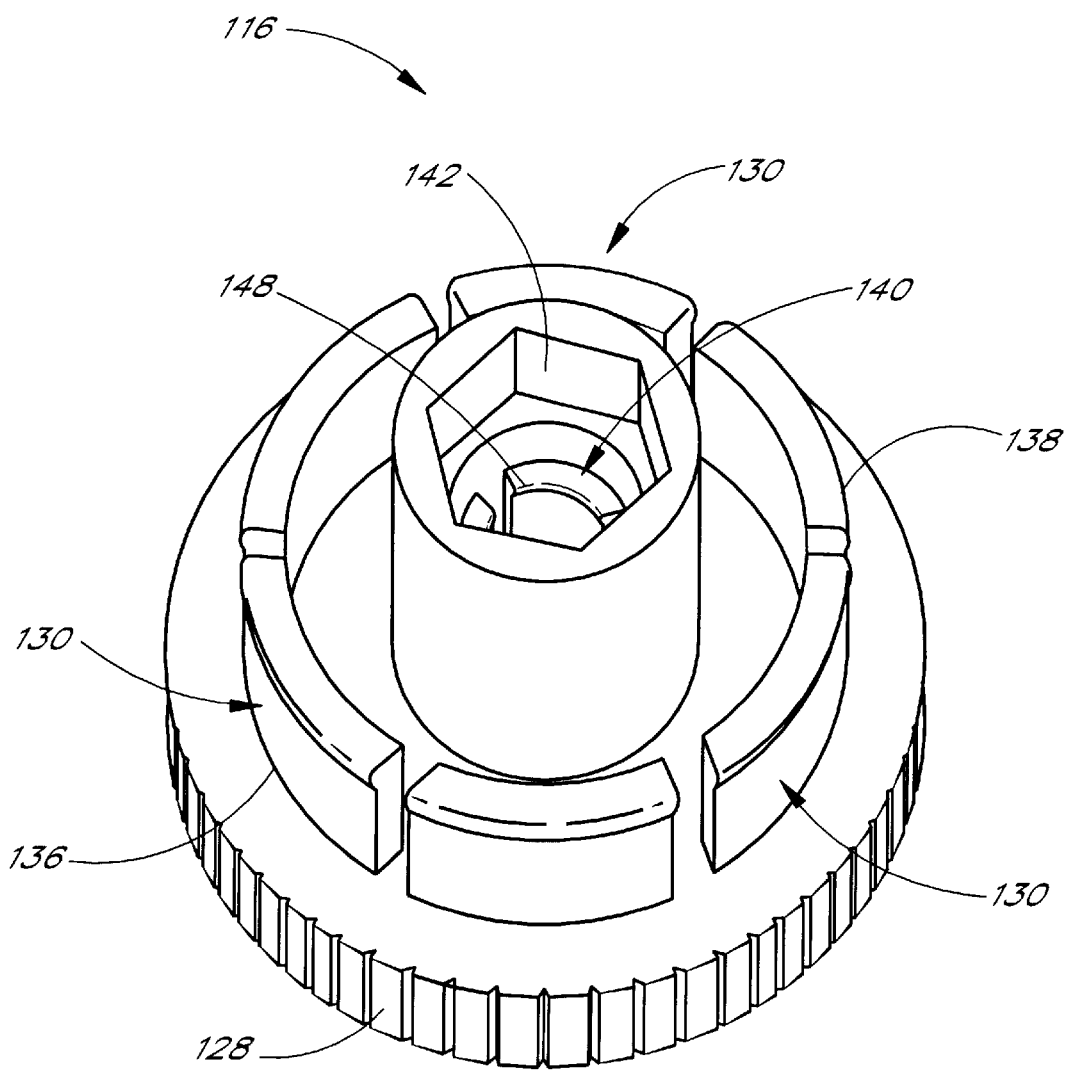
FIG. 10 is a perspective view of the carrier of FIG. 8.

Referring to FIGS. 8 to 10, and particularly to FIG. 8, another preferred embodiment of a dental implant assembly package/combination 110 constructed and assembled in accordance with the present invention includes a vial 112 and a dental implant assembly/kit 114 comprising a threaded implant carrier 116, an insertion tool screw 118, an insertion tool 119 and a threaded implant 120. A healing screw 121 may also be included in the dental implant assembly/kit 114. The carrier 116 reliably and releasably grips the insertion tool screw 118 and serves as a handle for transporting the dental implant 120 to a surgical site and facilitates insertion of the implant 120 into an osteotomy or alveolar cavity in the jawbone of a patient. The carrier 116 also reliably and releasably interfaces with the vial 112 to provide a detachable cap for the vial 112.

Preferably, the threaded implant carrier 116 (FIGS. 8 to 10) comprises an anterior section/cap 122, a medial section 124 and a posterior section 126. The anterior section/cap 122 is preferably generally cylindrical in shape and has a substantially central cylindrical cavity 180. Optionally, the outer curved surface 128 of the anterior section 122 may be ridged, grooved or knurled to provide a convenient gripping surface.

Preferably, the medial section 124 of the carrier 116 (FIG. 9) includes a generally cylindrical inner core 132 with a substantially central cylindrical cavity 182. The inner core 132 is in communication with the carrier anterior section 122. The carrier anterior section cavity 180 and the carrier medial section cavity 182 are preferably in communication with one another. In one preferred embodiment of the present invention, a healing screw 121 (FIG. 8) resides in the cavities 180 and 182, and a layer of adhesive paper 133 (FIG. 8) or the like is removably attached to the top of the anterior section/cap 122. The layer 133 prevents the healing screw 121 from falling out of the carrier 116. Optionally, the paper layer 133 may include a tab 135 to facilitate its removal from the carrier 116.

Referring to FIGS. 8 to 10, preferably, the carrier medial section 124 includes a plurality of vial-engaging fingers 130 for interfacing with the vial 112, and a plurality of screw-engaging fingers 140 for holding the insertion tool screw 118. The vial-engaging fingers 130 are in communication with and extend away from the carrier anterior section/cap 122 towards the carrier posterior section 126. The fingers 130 are spaced from and generally circumscribe the inner core 132.

Preferably, the vial-engaging fingers 130 (FIGS. 8 to 10) are flexible, and hence resiliently displaceable relative to the medial section inner core 132. In one preferred form of the present invention, the plurality of fingers 130 comprises six fingers. But as will be readily apparent to those of ordinary skill in the art, more or fewer fingers may be utilized with efficacy, as needed or desired, giving due consideration to the desired goal of providing a reliable and releasable interface with the vial 112 (FIG. 8). It is generally preferred to have three to six vial-interfacing fingers 130. Preferably, the fingers 130 are arranged in a substantially symmetrical fashion and substantially equidistantly spaced from their respective neighboring fingers. Of course, the fingers 130 may be alternatively spaced in a variety of configurations or patterns with efficacy, giving due consideration to the goal of providing a reliable and releasable interface with the vial 112. In one preferred embodiment of the present invention, the fingers 130 are integrally molded with the carrier 116.

Referring to FIGS. 8 to 10, preferably, each one of the vial-interfacing fingers 130 has a respective body portion 136 and a respective projecting or bulging bottom end 138. The finger body portions 136 are preferably spaced from the inner core 132 to create clearance space for the resilient displacement of the fingers 130. The finger body portions 136 are curved to generally follow the curvature of the inner core 132 and the vial 112 (FIG. 8) with which the carrier 116 mates.

The bottom ends 138 (FIGS. 8 to 10) of the respective fingers 130 project or bulge generally radially outwards relative to the inner core 132, and are generally thicker than the respective finger body portions 136. The finger bottom ends 138 are preferably spaced from the inner core 132 to create clearance space for the resilient displacement of the fingers 130. Preferably, the finger bottom ends 138 are curved to generally follow the curvature of the medial section inner core 132 and the vial 112 FIG. 8) with which the carrier 116 mates. The projection or bulging of the finger bottom ends 138 serves to form a detent mechanism for relative engagement with mating inner surfaces of a cylindrical vial. In particular, and as will be discussed in more detail later herein, the bulging or projecting of the finger bottom ends 138 cooperates with an annular or circumferential groove formed on the vial 112 (FIG. 8) to lock the carrier 116 into the vial 112.

The screw-engaging fingers 140 (FIGS. 9 and 10) are located within the medial section cavity 182 and are connected to an internal wall 183 (FIG. 9) of the cavity 182. Preferably, the fingers 140 are flexible, and hence resiliently displaceable relative to the internal wall 183 of the carrier medial section 124. In one preferred embodiment, the carrier 116 includes three fingers 140, but as will be readily apparent to those of ordinary skill in the art, more or fewer fingers may be utilized with efficacy, as needed or desired, giving due consideration to the desired goal of providing a reliable and releasable grip on the insertion tool screw 118 (FIG. 8). It is generally preferred to have three to six screw-engaging fingers 140. Preferably, the fingers 140 are arranged in a substantially symmetrical fashion and substantially equidistantly spaced from their respective neighboring fingers. Of course, the fingers 140 may be alternatively spaced, with efficacy, giving due consideration to the goal of providing a reliable and releasable grip on the insertion tool screw 118 (FIG. 8). Preferably, the fingers 140 extend in a direction away from the carrier anterior section 122. Alternatively, the fingers 140 may be configured to extend in the direction towards the carrier anterior section 122. In one preferred embodiment of the present invention, the fingers 140 are integrally molded with the carrier 116.

Referring to FIGS. 9 and 10, preferably, each one of the fingers 140 has a respective top end 144, a respective body portion 146, and respective bottom projecting or bulging end 148. The finger top ends 144 are attached to the carrier internal wall 183, and are preferably curved to generally follow the curvature of the internal wall 183. Functionally, the finger top ends 144 serve the purpose of attaching the respective screw-engaging fingers 140 to the carrier internal wall 183 and of spacing the respective displaceable body portions 146 and bottom ends 148 of the respective fingers 140 from the carrier internal wall 183.

Preferably, the body portions 146 (FIG. 9) of the screw-engaging fingers 140 extend in a direction away from the respective top ends 144. The finger body portions 146 are preferably spaced from the carrier internal wall 183 to create clearance space for the resilient displacement of the fingers 140. Preferably, the finger body portions 146 are curved to generally follow the curvature of the carrier internal wall 183 and the insertion tool screw 118 (FIG. 8) with which the carrier 116 mates.

Referring in particular to FIGS. 9 and 10, preferably, the bottom ends 148 of the respective screw-engaging fingers 140 project or bulge generally radially inwards into the cavity 182 of the carrier medial section 124, and are generally thicker than the respective finger body portions 146. The finger bottom ends 148 are preferably spaced from the carrier internal wall 183 to create clearance space for the resilient displacement of the fingers 140. Preferably, the finger bottom ends 148 are curved to generally follow the curvature of the carrier internal wall 183 and the insertion tool screw 118 (FIG. 8) with which the carrier 116 mates. The projection or bulging of the finger bottom ends 148 serves to form a detent mechanism for relative engagement with mating inner surfaces of an insertion tool screw or generally similar component of a dental implant assembly or kit. In particular, and as will be discussed in more detail later herein, the bulging or projecting of the finger bottom ends 148 cooperates with an annular or circumferential groove formed on the insertion tool screw 118 (FIG. 8) to lock the screw 118 into the carrier 116.

Preferably, and referring to FIGS. 9 and 10, the carrier posterior section 126 is generally cylindrical in shape and includes a substantially hexed central cavity 142. Preferably, the carrier posterior section hexed cavity 142 and the carrier medial section cylindrical cavity 182 are in communication. The hexed cavity 142 permits the carrier 116 to substantially irrotationally mate with the insertion tool 119 (FIG. 8), though those skilled in the art will readily comprehend that the cavity 142 may be alternately shaped, as required or desired.

The insertion tool screw 118 (FIG. 8), preferably, includes a head 150, a groove or notch 154, a body portion 156, and a lower threaded portion 152. Preferably, the top of the screw head 150 has a taper 158, in the direction moving away from the screw body portion 156, which assists in inserting the screw head 150 within the carrier screw-engaging fingers 140 (FIGS. 9 and 10). The screw head 150 also includes a substantially hexed socket (not shown) to receive a suitable insertable wrench. Preferably, the groove 154 is positioned below and proximate to the screw head 150. The groove 154 of the insertion tool screw 118 is preferably substantially circumferential or annular and is adapted to engage the bulging or projecting finger bottom ends 148 (FIGS. 9 and 10). The threaded portion 152 of the insertion tool screw 118 threadably connects the screw 118 to the dental implant 120 (FIG. 8).

Those skilled in the art will readily recognize that though the drawings illustrate the bulging finger bottom ends 148 (FIGS. 9 and 10) to be generally bulbous and the screw groove 154 (FIG. 8) to be generally circumferential or annular, alternate configurations may be employed with equal efficacy, giving due consideration to the goals of providing a reliable and releasable mechanical lock for holding the implant 120. For example, other recesses, either continuous or discrete, may be formed on the insertion tool screw 118 to provide a locking niche for the fingers 140. The groove or locking niche 154 may also be placed on any one of the components forming an implant assembly or package. For example, the groove 154 may be placed on the insertion tool 119. The implant assembly 114, as illustrated in FIG. 8 includes the healing screw 121, the insertion tool screw 118, the insertion tool 119, and the implant 120, though it can include fewer or more components. Also, one or more components may be combined, as desired, to form an integral assembly.

Preferably, the insertion tool 119 (FIG. 8) has a substantially hexagonal upper portion 160 which is dimensioned to form a substantially irrotational fit in the substantially hexed cavity 142 of the carrier posterior section 126. The insertion tool 119 also includes a substantially central through cavity (not shown) which permits the insertion tool screw 118 to traverse through the insertion tool and threadably mate with the implant 120. This insertion tool through cavity can also include at its lower end a substantially hexagonal socket (not shown) which allows substantially irrotational mating between the insertion tool 119 and the implant 120.

While the present invention may be used with a wide variety of dental implants, a very satisfactory and widely used threaded dental implant 120 is shown in FIG. 8. The implant 120 includes a threaded body or root portion 162, a generally hexagonal post 164 at the exposed top end 166, and a threaded socket 168 originating from the exposed end 166 and into the body portion 162. The implant body portion 62 is adapted to threadably engage an osteotomy or alveolar cavity in the jawbone of a patient. In the assembled state of the dental implant assembly/kit 114, the implant hexagonal post 164 mates with the insertion tool 119 to provide a substantially irrotational engagement. Also, as is known in the art, the hexagonal post 164 is configured to substantially irrotationally mate with a hexagonal cavity of an abutment (not shown) on which the final prosthesis (not shown) is mounted. In the assembled state of the dental implant assembly/kit 114, the threaded portion 152 of the insertion tool screw 118 is threadably engaged with the threaded socket 168 of the implant 120, thereby permitting the carrier 116 to hold the implant 120 via the insertion tool screw 118. The implant body portion 162 may include a passage 169 formed therethrough to permit in-growth of bone and tissue for locking or anchoring the implant in the osteotomy following installation. The implant body portion 162 may further include a pair of cutting edges 186 having recesses 188 (only one of each is visible in FIG. 8)

Referring to FIG. 8, the packaging vial 112 preferably comprises an open end 170, a closed end 171 and a generally cylindrical side wall 172 to form a hollow cavity 173 to receive the dental implant assembly/kit 114. Preferably, the side wall 172 includes a tapered inner surface 176 proximate to the open end 170 culminating in an inner surface 178 with a generally circumferential or annular groove or notch 174. The groove 174 is preferably spaced from the tapered inner surface 176. The tapered surface 176 facilitates the insertion and removal of the vial-engaging flexible fingers 130 through the vial open end 170. The groove 174 is configured and positioned to receive the projecting or bulging bottom ends 138 of the fingers 130 to provide a mechanical lock between the carrier 116 and the vial 112. Though the projecting or bulging finger bottom ends 138 are shown in the drawings (FIGS. 8 to 10) as being generally bulbous and the vial groove 174 to be generally circumferential and annular, alternate configurations may be employed with equal efficacy, giving due consideration to the goals of providing a reliable and releasable lock between the implant carrier 116 and the vial 112. For example, other recesses, either continuous or discrete, may be formed on the vial inner surface 178 to provide a locking niche for the carrier fingers 130. In the assembled state of the dental implant package 110, the carrier anterior section/cap 122 serves as a removable cap for the vial 112, thus providing a container for the dental implant 120.

The threaded implant carrier 116 (FIGS. 8 to 10) is preferably fabricated from a thermoplastic material, though other suitable plastics, rubbers, metals, alloys and ceramics may be utilized with efficacy, giving due consideration to the goals of providing reliable and releasable attachment to the carrier 116. In one preferred form of the invention, the implant carrier 116 is fabricated from a nylon such as 25% glass-reinforced nylon or ultramid B3WG5 nylon 6. Alternatively, the carrier fingers 130 and/or 140 may be fabricated from a material different than the rest of the carrier 116, as needed or desired, giving due consideration to the goals of providing reliable and releasable attachment to the carrier 116.

Preferably, and referring to FIG. 8, the dental implant 120, the healing screw 121, the insertion tool screw 118, and the insertion tool 119 are fabricated from pure titanium or a titanium alloy, which are compatible with bone, fixtures, tools, and the ultimate prosthesis, as well as being innocuous in use over time. Of course, the dental implant 120, the healing screw 121, the insertion tool screw 118, and the insertion tool 119 may be fabricated from or coated with other suitable metals, alloys, allographic materials, liquid crystal polymers (LCP) and ceramics, as required or desired, giving due consideration to one or more of the goals of providing bio-compatibility, inertness, corrosion-resistance and durability. The vial 112 (FIG. 8) is, preferably, fabricated from a light-weight, durable, clear plastic, though other materials may be used with equal efficacy, giving due consideration to the goals of providing reliable and releasable attachment to the carrier 116.

In one form of the present invention the threaded implant carrier 116 (FIGS. 8 to 9) has an overall length of about 0.710 inches and a maximum diameter between about 0.510 inches and about 0.530 inches. The vial-engaging fingers 130 have a length of about 0.189 inches and are arranged so that their respective body portions 136 form an outer diameter of about 0.427 inches. The screw-engaging fingers 140 have a length of about 0.113 inches. The finger top ends 144 and finger body portions 146 generally envelop a cylindrical region with a diameter of about 0.098 inches. The finger bottom ends 148 generally envelop a cylindrical region with a diameter of about 0.080 inches, and extend about 0.009 inches further inwards relative to the finger body portions 146. Preferably, when the fingers 140 are flexed, during engagement and disengagement with the insertion tool screw 118, they can provide an interference slip of up to about 15%. Those skilled in the art will readily recognize that the carrier 116 of the present invention may be sized and dimensioned in alternate ways with equal efficacy, giving due consideration to the goals of providing reliable and releasable attachment to the carrier 116.

Referring to FIGS. 8 to 9, the threaded implant carrier 116 of the present invention provides several benefits and advantages over conventional carriers by incorporating flexible fingers 130 and 140 to interface with the vial 112 and the insertion tool screw 118, respectively. Advantageously, the screw-engaging carrier fingers 140 can engage the insertion tool screw 118 by a redundant latching mechanism which is a combination of providing a mechanical lock and applying a compressive generally radial force. The mechanical lock is provided by the engagement of the bulging or projecting bottom ends 148 of the respective fingers 140 with the groove 154 of the insertion tool screw 118. The radial compressive force (interference fit) is provided due to the outward flexing of the resilient fingers 140 when the screw 118 is captured in the carrier 116. Advantageously, the fingers 140 are only slightly flexed in the assembled state of the dental implant assembly 114 since the resilient displacement of the fingers 140 is, in one preferred embodiment, only about 0.051 mm (0.002 inches) when the screw 118 is gripped in the carrier 116. Desirably, this minimizes the "deformation" or "pre-stressing" of the fingers 140 in the assembled state and permits a substantially long on-the-shelf and storage life for the dental implant package 110. It will be apparent to those skilled in the art that the present invention may be practiced with the carrier fingers 140 configured to apply less, more or no radial compressive force on the screw 118, as required or desired, giving due consideration to the goals of providing reliable fixturing between the carrier 116 and the screw 118 which is concurrently releasable by applying a predictable and/or low level of force. Of course, in the latter case of no radial compressive force, the fingers 140 will be substantially unflexed in the assembled state of the dental implant assembly/kit 114.

The resiliency of the fingers 140 permits insertion and removal of the insertion tool screw 118 from the carrier 116. During the insertion of the screw 118 in the carrier 116, preferably via the carrier posterior section 126, the fingers 140 are initially flexed generally radially outwards to receive the screw head 150. The tapered surface 158 of the screw head 150 facilitates the insertion of the insertion tool screw 118 in the carrier fingers 140. The fingers 140 are then flexed generally radially inwards until the projecting finger bottom ends 148 lock into the screw groove 154. During the removal of the screw 118 from the carrier 116, preferably via the carrier posterior section 126, again the fingers 140 are flexed generally radially outwards as the bulging or projecting finger bottom ends 148 slip out of the screw groove 154. The fingers 140 are then resiliently displaced inwards to their unflexed state as they release the screw head 150, hence allowing detachment of the insertion tool screw 118 from the carrier 116. Advantageously, the preferred generally bulbous shape of the finger bottom ends 148, provides a camming action, during removal (and insertion) of the screw 118 from the carrier 116, that facilitates this same removal (and insertion).

Advantageously, the vial-interfacing fingers 130 (FIGS. 8 to 10) provide a reliable mechanical lock between the carrier 116 and the vial 112 with the finger projecting ends 138 engaging the vial groove 174. In this manner, the carrier 116 also provides a cap for the vial 112 with the carrier anterior section/cap 122 seated at the vial open end 170. During insertion of the carrier 116 in the vial cavity 173, the fingers 130 are flexed inwards as they slide over the tapered inner surface 176 of the vial side wall 172 and then over the flat inner surface 178. Advantageously, this tapering of the inner surface 176 facilitates in the insertion of the carrier 116 in the vial cavity 173. The fingers 130 are then flexed outwards, preferably close to their unflexed state, as the finger projecting or bulging bottom ends 138 engage the vial groove or recess 174 to form a positive lock between the carrier 116 and vial 112. It is preferred that this engagement between the fingers 130 and the vial groove 174 provide a lock or latch with a minimal amount of interference fit. Advantageously, such an engagement creates a reliable fixturing between the carrier 116 and vial 112 which is concurrently releasable by applying a predictable and minimal level of force. This is convenient when the dental assembly/lit 114 is removed from the vial 112. Additionally, since the "pre-stressing" or "deformation" of the fingers 130 in the assembled state is preferably minimal, it reduces the possibility of the fingers 130 losing their resilience during a long on-the-shelf and/or storage life. Desirably, the preferred generally bulbous shape of the finger projecting bottom ends 138 provides a camming action during insertion and removal of the carrier 116 in the vial cavity 173. Also, the degree of the interference fit between the carrier fingers 130 and the vial 112 can be increased or decreased, as required or desired, giving due consideration to the goals of providing a reliable fixturing between the carrier 116 and the vial 112 such that the carrier 116 is manually releasable from the vial 112 by applying a generally predictable low level of force.

In use, and referring to FIGS. 8 to 10, the dental implant assembly/kit 114 is removed from the dental implant package 110 by manually gripping the carrier anterior section/cap 122 and pulling it. During this removal, the vial-interfacing fingers 130 are released from their lock in the vial groove 174. The fingers 130 are initially flexed inwards as the finger projecting bottom ends 138 slide out of the vial groove 174 and over the part of the vial flat inner surface 178 between the vial groove 174 and the vial tapered inner surface 176. The fingers 130 then begin to flex in the opposite direction as the finger projecting bottom ends 138 slide over the vial tapered inner surface 176. As the finger projecting bottom ends 138 are extracted from the vial cavity 173 through the vial open end 170, the fingers 130 return to their generally unflexed state. Thus, the dental implant assembly/kit 114 is removed from the vial 112. The healing screw 121 can be removed from the carrier 116 before or after the dental implant assembly 114 is removed from the vial 112.

At this stage, the carrier 116 (FIGS. 8 to 10) is reliably and releasably holding the insertion tool screw 118 which in turn is attached to the threaded implant 120. The dental implant assembly/kit 114 is transported to the surgical site with the carrier anterior section 122 being manually held. Since the fingers 140 reliably grip the screw 118, the implant 120 is prevented from coming loose from the dental implant assembly/kit 114. While still manually holding the carrier anterior section 122, the threaded implant 120 is inserted into an osteotomy in the patient's jawbone and by rotating the carrier anterior section 122 the implant 120 is "threaded" into the osteotomy. The carrier 116 may be used to drive the implant 120 fully in the osteotomy, after which it can be detached from the screw 118. During removal of the carrier 116 from the screw 118 the carrier fingers 140 flex in the manner that has been described herein above and permit the release of the screw 118 from the carrier 116. The driving force for implant insertion is transferred from the carrier 116 to the implant 120 via the insertion tool 119 which is at its hexagonal upper portion 160 engaged in the carrier hexed cavity 142 and at its lower end substantially irrotationally mated with the implant 120. In some cases, a suitable wrench or ratchet (not shown), which engages the insertion tool screw 118 and/or the insertion tool 119, may be used to further seat the implant 120 in the appropriate subgingival position in the osteotomy. The carrier 116, insertion tool screw 118 and the insertion tool 119 are typically discarded at this stage and the healing screw 121 is used to cap the implant 120.

The threaded implant carrier 116 (FIGS. 8 to 10) may also be configured utilizing only one of the pair of sets of fingers 130 and 140. For example, the carrier 116 may be constructed with a plurality of vial-engaging fingers 130 to provide a cap for the vial 112 and employ some other attachment scheme to hold the insertion tool screw 118. Alteratively, the carrier may be formed with a plurality of screw-gripping fingers 140 to grip the insertion tool screw 118 and utilize a conventional engaging scheme to cap the vial 112.

The utility of the present invention will be readily apparent to those skilled in the art. The implant carrier of the present invention provides improved means for holding a dental implant in a dental implant package, during transport of the implant to a surgical site and during insertion of the implant in an osteotomy. The implant carrier also, desirably, provides an improved releasable interface with a packaging vial and serves as a cap for the vial without the need for additional interfacing components to be included in the dental implant package. Advantageously, the implant carrier of the present invention can be adapted for use in conjunction with a wide variety of dental screws, dental implants, such as various types of cylindrical and threaded implants, among other dental components.

While the components of the present invention have been described with a certain degree of particularity, it is manifest that many changes may be made in the specific designs, constructions and methodology hereinabove described without departing from the spirit and scope of this disclosure. It should be understood that the invention is not limited to the embodiments set forth herein for purposes of exemplification, but is to be defined only by a fair reading of the appended claims, including the full range of equivalency to which each element thereof is entitled.

What is claimed is:

1. A dental implant container for receiving and supporting a healing screw having a threaded portion and a head, and an implant having a body portion adapted to be received in an osteotomy and a threaded socket at one end sized and configured to threadably engage said threaded portion of said healing screw, comprising:
    a carrier including a first plurality of flexible fingers and a second plurality of flexible fingers, said first plurality of flexible fingers being adapted to releasably grip said head of said healing screw; and
    a vial having an inner surface in mating engagement with respective projecting portions of said second plurality of flexible fingers to removably cap an open end of said vial.

2. The dental implant container of claim 1, wherein said first plurality of flexible fingers is adapted to grip said healing screw by applying a substantially radial compressive force.

3. The dental implant container of claim 1, wherein said first plurality of flexible fingers is adapted to form an interference fit with said healing screw.

4. The dental implant container of claim 1, wherein said first plurality of flexible fingers include respective inner tapered surfaces which are adapted to latch with a tapered peripheral wall of said head of said healing screw.

5. The dental implant container of claim 1, wherein said carrier further includes a protrusion generally circumscribed by said first plurality of flexible fingers and adapted to engage a wrench-receiving cavity in said head of said screw to stabilize the grip of said first plurality of flexible fingers on said head of said screw.

6. The dental implant container of claim 1, wherein said projecting portions of said second plurality of flexible fingers mechanically lock into said vial.

7. The dental implant container of claim 1, wherein said projecting portions of said second plurality of flexible fingers mechanically lock into a groove formed on said inner surface of said vial.

8. The dental implant container of claim 7, wherein said groove is substantially circumferential.

9. The dental implant container of claim 1, wherein said second plurality of flexible fingers form an interference fit with said inner surface and a groove formed on said inner surface.

10. The dental implant container of claim 1, wherein said first plurality of flexible fingers and/or said second plurality of flexible fingers are substantially equidistantly and symmetrically spaced.

11. The dental implant container of claim 1, wherein said first plurality of flexible fingers comprises between three and six fingers.

12. The dental implant container of claim 1, wherein said second plurality of flexible fingers comprises between three and six fingers.

13. The dental implant container of claim 1, wherein said vial includes a tapered surfaced proximate to said open end of said vial to facilitate insertion and/or removal of said carrier from said vial.

14. The dental implant container of claim 1 in combination with said healing screw and said dental implant forming a dental package.

15. A dental implant assembly, comprising:
a dental implant having a body portion adapted to be received in an osteotomy and a threaded socket at one end;
a screw having a head and a threaded portion threadably engaged with said threaded socket of said dental implant; and
a carrier including a plurality of flexible fingers for releasably engaging said screw and thereby serving as a holder for holding and transporting said implant.

16. The dental implant assembly of claim 15 in combination with a vial for packaging said dental implant assembly.

17. The dental implant assembly of claim 16, wherein said carrier further includes a second plurality of flexible fingers for engaging said vial.

18. The dental implant assembly of claim 17, wherein said second plurality of flexible fingers include respective projecting portions for mechanically locking into a groove of said vial to releasably interface with said vial and provide a cap at an open end of said vial.

19. The dental implant assembly of claim 15, wherein said plurality of flexible fingers form a mechanical lock with said screw.

20. The dental implant assembly of claim 15, wherein said plurality of flexible fingers form an interference fit with said screw.

21. The dental implant assembly of claim 15, wherein said screw comprises an insertion tool screw.

22. The dental implant assembly of claim 15, wherein said screw comprises a healing screw.

23. The dental implant assembly of claim 15, wherein said plurality of flexible fingers comprises between three and six fingers.

24. The dental implant assembly of claim 15, wherein said body portion of said implant is threaded.

25. The dental implant assembly of claim 15, wherein said body portion of said implant is generally cylindrical and generally smooth.

26. A dental implant assembly, comprising:
a dental implant having a body portion adapted to be received in an osteotomy and a threaded socket at one end;
a healing screw having a head and a threaded portion threadably engaged with said threaded socket of said dental implant to cap said threaded socket of said implant; and
a carrier releasably engaged with said healing screw and including a plurality of flexible fingers with respective projecting portions, said projecting portions being releasably interfaced with one or more recesses formed on an inner surface of a vial whereby said dental implant is able to be supported within said vial.

27. The dental implant assembly of claim 26, wherein said carrier further includes a second plurality of flexible fingers to releasably grip said head of said screw.

28. The dental implant assembly of claim 27, wherein said carrier further includes a protrusion generally circumscribed by said second plurality of flexible fingers and in engagement with a wrench-receiving cavity in said head of said screw to stabilize the grip of said second plurality of flexible fingers on said head of said screw.

29. The dental implant assembly of claim 26, wherein said projecting portions of said plurality of flexible fingers mechanically lock into said vial.

30. The dental implant assembly of claim 26, wherein said projecting portions of said plurality of flexible fingers mechanically lock into said one or more recesses of said vial.

31. The dental implant assembly of claim 26, wherein said plurality of flexible fingers form an interference fit with said inner surface and said one or more recesses of said vial.

32. The dental implant assembly of claim 26, wherein said plurality of flexible fingers are substantially equidistantly and symmetrically spaced.

33. The dental implant assembly of claim 26, wherein said plurality of flexible fingers comprises between three and six fingers.

34. The dental implant assembly of claim 26, wherein said one or more recesses of said vial form a substantially circumferential groove.

35. The dental implant assembly of claim 26, wherein said vial includes a tapered surface proximate to an open end of said vial to facilitate insertion and/or removal of said carrier from said vial.

36. The dental implant assembly of claim 26, wherein said vial includes an open end which is capped by said carrier.

37. The dental implant assembly of claim 26, wherein said body portion of said implant is generally cylindrical and generally smooth.

38. A carrier for a dental implant package, said carrier including a first plurality of flexible fingers and a second plurality of flexible fingers, said first plurality of flexible fingers being adapted to releasably grip a dental screw adapted to threadably engage a dental implant, said second plurality of flexible fingers being adapted to releasably interface with an inner surface of a vial to enclose said screw and said dental implant within said vial.

39. The carrier of claim 38 in combination with said screw and said implant to form a dental assembly.

40. The carrier of claim 38, wherein said carrier further includes a protrusion generally circumscribed by said first plurality of flexible fingers and being adapted to engage a wrench-receiving cavity in a head of said screw to stabilize the grip of said first plurality of flexible fingers on said screw.

41. The carrier of claim 38, wherein said second plurality of flexible fingers include respective projecting portions for mechanically locking into a groove of said vial to cap an open end of said vial.

42. The carrier of claim 38, wherein said screw comprises an insertion tool screw for facilitating the insertion of said implant into said osteotomy.

43. The carrier of claim 38, wherein said screw comprises a healing screw for capping said implant in said osteotomy.

44. The carrier of claim 38, wherein said implant comprises a threaded implant.

45. The carrier of claim 38, wherein said implant comprises a cylindrical implant.

46. A carrier for a dental implant kit, said carrier including a plurality of flexible fingers which are adapted to releasably grip a head of a healing screw adapted to threadably engage a dental implant, said carrier further including a protrusion generally circumscribed by said plurality of flexible fingers and being adapted to engage a wrench-receiving cavity in said head of said screw to stabilize the grip of said plurality of flexible fingers on said head of said screw, said carrier having means for manually holding said carrier to transport said healing screw and said implant to an osteotomy.

47. The carrier of claim 46, wherein said carrier further includes a second plurality of flexible fingers being adapted to releasably interface with a groove on an inner surface of a vial to cap an open end of said vial and enclose said healing screw and said dental implant within said vial.

48. The carrier of claim 47, wherein said second plurality of flexible fingers include respective projecting portions for mechanically locking into said groove of said vial.

49. The carrier of claim 46, wherein said plurality of flexible fingers comprises between three and six fingers.

50. A dental implant package, comprising:
   a dental implant assembly comprising:
      a dental implant carrier;
      a healing screw; and
      a dental implant; and
   a packaging vial including an open end, a closed end and a side wall therebetween, said side wall having one or more grooves on an inner surface to releasably engage respective projecting portions of a plurality of flexible fingers of said dental implant carrier to cap said open end of said vial and to enclose said dental implant assembly substantially within said vial, said inner surface of said vial including a tapered surface adjacent to said open end to facilitate easy insertion and removal of said dental implant assembly into/from said vial.

51. The vial of claim 50, wherein said carrier includes a second plurality of flexible fingers to releasably grip a head of said healing screw.

52. A carrier for a dental implant package, comprising:
   an anterior section being generally cylindrical in shape and having a generally cylindrical cavity, said anterior section being adapted to serve as a holder by providing a holding surface for manual manipulation of said anterior section, said anterior section being sized and configured to serve as a cap for a vial of said dental implant package;
   a medial section including a first plurality of flexible fingers and a first generally cylindrical spacing member and a second generally cylindrical spacing member, said first spacing member having a generally hexagonal cavity in communication with said anterior section cavity and with a generally cylindrical cavity of said second spacing member, said first plurality of flexible fingers being in communication with and extending away from said anterior section of said carrier, said first plurality of flexible fingers being spaced from and generally circumscribing said first spacing member which is in communication with said anterior section, said first plurality of flexible fingers being resiliently displaceable relative to said first spacing member, said first plurality of flexible fingers including respective body portions in communication with said anterior section and respective projecting or bulging bottom ends, said bottom ends projecting generally radially outwards relative to said first spacing member and being generally thicker than said body portions, said bottom ends being sized and configured to releasably mechanically lock into a substantially circumferential groove formed on an inner surface of said vial of said dental implant package; and
   a posterior section including a second plurality of flexible fingers to form a cavity and a protrusion within said posterior section cavity, said second plurality of flexible fingers being in communication with and extending away from said second spacing member of said medial section, said second plurality of flexible fingers being resiliently displaceable relative to said second spacing member, said second plurality of flexible fingers being sized and configured to releasably grip a head of a healing screw of said dental implant package to hold a dental implant attached to said healing screw within said vial, said protrusion being adapted to engage a wrench-receiving cavity in said head of said healing screw to stabilize the grip of said second plurality of flexible fingers on said head of said screw.

53. A dental implant package, comprising the carrier of claim 52 in combination with said dental implant, said healing screw and said vial.

54. A dental implant combination, comprising:
   a carrier including a first plurality of flexible fingers and a second plurality of flexible fingers;
   a healing screw having a threaded portion and a head being sized and configured to be releasably gripped by said first plurality of flexible fingers;
   an implant having a body portion adapted to be received in an osteotomy and a threaded socket at one end sized and configured to threadably engage said threaded portion of said healing screw; and
   a vial having an inner surface adapted to matingly engage respective projecting portions of said second plurality of flexible fingers for capping an open end of said vial and for supporting said healing screw and said implant within said vial.

55. The dental implant combination of claim 54, wherein said first plurality of flexible fingers are sized and configured to grip said healing screw by applying a substantially radial compressive force.

56. The dental implant combination of claim 54, wherein said first plurality of flexible fingers are sized and configured to form an interference fit with said healing screw.

57. The dental implant combination of claim 54, wherein said first plurality of flexible fingers include respective inner tapered surfaces which are adapted to latch with a tapered peripheral wall of said head of said healing screw.

58. The dental implant combination of claim 54, wherein said carrier further includes a protrusion generally circumscribed by said first plurality of flexible fingers and adapted to be received in a wrench-receiving cavity in said head of said screw to stabilize the grip of said first plurality of flexible fingers on said head of said screw.

59. The dental implant combination of claim 54, wherein said projecting portions of said second plurality of flexible fingers are adapted to mechanically lock into said vial.

60. The dental implant combination of claim 54, wherein said projecting portions of said second plurality of flexible fingers are adapted to mechanically lock into a groove formed on said inner surface of said vial.

61. The dental implant combination of claim 60, wherein said groove is substantially circumferential.

62. The dental implant combination of claim 54, wherein said second plurality of flexible fingers are adapted to form an interference fit with said inner surface and a groove formed on said inner surface.

63. The dental implant combination of claim 54, wherein said first plurality of flexible fingers and/or said second plurality of flexible fingers are substantially equidistantly and symmetrically spaced.

64. The dental implant combination of claim 54, wherein said first plurality of flexible fingers comprises between three and six fingers.

65. The dental implant combination of claim 54, wherein said second plurality of flexible fingers comprises between three and fingers.

66. The dental implant combination of claim 54, wherein said vial includes a tapered surfaced proximate to said open end of said vial to facilitate insertion and/or removal of said carrier from said vial.

67. The dental implant combination of claim 54, wherein said body portion of said implant is generally cylindrical and generally smooth.

68. A method of delivering a dental implant to a surgical site and seating said dental implant in an osteotomy, comprising the steps of:
 holding said dental implant by gripping a carrier having a plurality of flexible fingers releasably engaged with a screw threadably engaged with said dental implant;
 transporting said dental implant to said surgical site;
 inserting said dental implant in said osteotomy;
 manipulating said carrier to seat said dental implant in said osteotomy; and
 disengaging said carrier from said screw by pulling and/or bending said carrier to release the grip of said plurality of flexible fingers on said screw.

69. The method of claim 68, further comprising the step of removing said dental implant from a packaging vial wherein said carrier serves as a cap for said vial and further includes a second plurality of flexible fingers releasably engaged with an inner surface of said vial.

70. The method of claim 69, wherein said step of removing said dental implant from a packaging vial includes the step of pulling said carrier to disengage respective projecting portions of said second plurality of fingers from mating engagement with said inner surface of said vial.

71. The method of claim 68, wherein said step of manipulating said carrier comprises the step of pushing said carrier to press-fit said dental implant in said osteotomy.

72. The method of claim 68, wherein said step of manipulating said carrier comprises the step of rotating said carrier to thread said dental implant in said osteotomy.

\* \* \* \* \*

UNITED STATES PATENT AND TRADEMARK OFFICE
CERTIFICATE OF CORRECTION

PATENT NO. : 6,217,332 B1
DATED : April 17, 2001
INVENTOR(S) : Ajay Kumar

Page 1 of 1

It is certified that error appears in the above-identified patent and that said Letters Patent is hereby corrected as shown below:

<u>Claim 65,</u>
Line 23, "three and fingers." should read -- three and six fingers.

Signed and Sealed this

Sixteenth Day of April, 2002

Attest:

Attesting Officer

JAMES E. ROGAN
*Director of the United States Patent and Trademark Office*